(12) United States Patent
Kim et al.

(10) Patent No.: US 7,915,276 B2
(45) Date of Patent: Mar. 29, 2011

(54) BERBERRUBINE DERIVATIVES HAVING ANTIFUNGAL ACTIVITIES

(75) Inventors: Sung Uk Kim, Daejeon (KR); Ki Duk Park, Daejeon (KR); Jae Sun Moon, Daejeon (KR); Tae Hoon Kang, Daejeon (KR); Young Kook Kim, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 251 days.

(21) Appl. No.: 11/911,371

(22) PCT Filed: Nov. 6, 2006

(86) PCT No.: PCT/KR2006/004607
§ 371 (c)(1),
(2), (4) Date: Oct. 12, 2007

(87) PCT Pub. No.: WO2007/094548
PCT Pub. Date: Aug. 23, 2007

(65) Prior Publication Data
US 2010/0292476 A1    Nov. 18, 2010

(30) Foreign Application Priority Data

Feb. 14, 2006  (KR) .................... 10-2006-0014146

(51) Int. Cl.
*A61K 31/4741*    (2006.01)
*C07D 491/12*    (2006.01)

(52) U.S. Cl. ........................... 514/280; 546/48
(58) Field of Classification Search .............. 546/48; 514/280
See application file for complete search history.

(56) References Cited

U.S. PATENT DOCUMENTS 6,030,978 A * 2/2000 Kim et al. .............. 514/280

FOREIGN PATENT DOCUMENTS

WO    WO 00/37468    6/2000
WO    WO 03/051875    6/2003

OTHER PUBLICATIONS

Mizuta, Hiroyuki et al.: "Smiles Rearrangement in Isoquinolinium Salts", *Chem. Pharm. Bull*, vol. 35 (1987) pp. 2238-2242.
Park, Ki Duk et al.: << Synthesis of 13-(substituted benzy) berberine and berberrubine derivaties as antifungal agents >>, *Bioorganic & Medicinal Chemistry Letters*, 16 (2006), pp. 3913-3916.

* cited by examiner

*Primary Examiner* — Charanjit S Aulakh
(74) *Attorney, Agent, or Firm* — Frommer Lawrence & Haug LLP; Ronald R. Santucci

(57) ABSTRACT

The present invention relates to a berberrubine derivative having superior antifungal activity, more particularly to a berberrubine derivative having activity against chitin synthase, which participates in the synthesis of chitin and is essential in the growth of fungi, and having a potent antifungal activity against human pathogenic fungi.

6 Claims, No Drawings

BERBERRUBINE DERIVATIVES HAVING ANTIFUNGAL ACTIVITIES

TECHNICAL FIELD

The present invention relates to a berberrubine derivative having superior antifungal activity, more particularly to a berberrubine derivative having inhibitory activity against chitin synthase, which participates in the synthesis of chitin and is essential in the growth of fungi, and having potent antifungal activity against human pathogenic fungi, which is represented by the following formula (1):

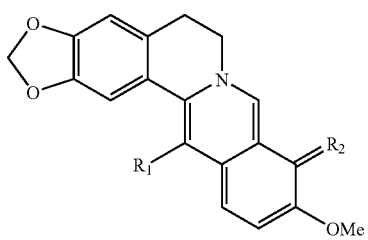

(1)

wherein $R_1$ is benzyl or substituted benzyl; $R_2$ is ketone (=O) or OR, wherein R is $C_3$-$C_{10}$ alkyl, $C_1$-$C_{10}$ haloalkyl, $C_1$-$C_{10}$ hydroxyalkyl, $C_2$-$C_{10}$ alkenyl, benzyl or substituted benzyl; and the substituted benzyl has 1 to 4 substituents selected from halogen atom, $C_1$-$C_6$ alkyl, $C_1$-$C_6$ haloalkyl, $C_1$-$C_6$ alkoxy and $C_1$-$C_6$ haloalkoxy.

BACKGROUND ART

Human mycoses can be largely classified into cutaneous mycoses and systemic mycoses and the latter is more of concern. Despite the advancement in medical technologies during the past 20 years, the systemic mycoses are on the increase. The mycoses occur frequently in patients whose immune functions have been weakened due to excessive use of antibacterial agents, organ transplantations, long-term medication of anti-cancer medicines, aging, and AIDS, etc., or in patients who rely on catheters or prosthetic devices (Beck-Sague, C. M. et al. *J. Infect. Dis.,* 167, 1247-1251, 1993; Diamond, R. D., *Rev. Infect. Dis.,* 13, 480-486, 1991). Moreover, according to a report, about 40% of the patients who are hospitalized with infection die of mycoses, with the representative opportunistic pathogens being *Candida albicans, Candida glabrata, Candida krusei, Cryptococcus neoformans,* etc. (Strenberg, S., *Science,* 266, 1632-1634, 1994).

The occurrence of invasive candidiasis has increased by ten-fold. The invasive aspergillosis, which frequently occurs in lungs, is the primary cause of death for the bone marrow-transplanted patients (Pannuti, C. et al., *Cancer,* 69, 2653-2662, 1992) and the death caused by aspergillosis is on the increase. Thus, the necessity of a new antifungal agent is ever increasing. Since most of the mycoses caused by opportunistic infection are hard to diagnose with the common blood culture, even the treatment of severe immunodeficiency patients is performed depending only on experiences (Walsh, T. J. et al., *Rev. Infect. Dis.,* 13, 496-503, 1991). Most mycoses have been known to occur mainly in patients with weakened immune functions. But, since the earthquake that outbroke in 1994 around Los Angeles (LA), hundreds of mycoses cases had occurred for 3 consecutive years as the spores that had been buried in earth were scattered into the air. During this period, the mortality increased by more than ten times, and with this incidence, it was reported that the fear of mycoses was no longer confined to the patients with weakened immune functions (Strenberg, S., *Science,* 266, 1632-1634, 1994). The increase of mycoses is gaining the attentions of researchers, yet the prevention of the conditions is not an easy task. In particular, due to the lack of an antifungal agent having superior efficiency with little toxicity, the amphotericin B, which was developed in the 1960s, is still being used in clinical treatment of systemic mycoses in spite of its high toxicity (Georgopadakou, N. H. et al., *Science,* 264, 371-373, 1994). Moreover, the occurrence of fungal strains resistant to existing antifungal agents is on the increase (Rex, J. H. et al., *Antimicrob. Agents Chemother.,* 39, 1-8, 1995).

Also, the number of cases where a non-pathogenic strain turns into pathogenic strain in patients with weakened immune functions is increasing. Since pathogenic fungi are hard to culture and mostly reproduce asexually, systematic researches on pathogenic fungi have long been deferred (Strenberg, S., *Science,* 266, 1632-1634, 1994).

At present, the antifungal agents used for clinical purposes are mostly polyenes, azole derivatives, allylamines and thiocarbamates. They either interact with ergosterol, the cell membrane component of fungi, or inhibit the synthesis of ergosterol. However, since most of the compounds have fungistatic activity and the fungi resistant to them appear very frequently, the development of new antifungal agents has been on constant demand. For the treatment of systemic fungal infections, amphotericin B is still widely used because of the lack of superior medicines. However, since it is highly nephrotoxic and may induce pernicious anemia when administered repeatedly, preparation forms developed using lipid complex, colloidal dispersion and liposome to reduce the toxicity were also reported (Kauffman, C. A. et al., *Drugs,* 53, 539-549, 1997).

Since fungi have cell walls that are different from those of mammals, the cell wall of fungi has long been seen as a good target. The cell wall of fungi maintains the cell structure, prevents the cell from being destroyed by osmosis while participating in the transfer of macromolecules. The cell wall of fungi is made up of chitin, α-glucan, β-glucan, mannan, etc. Of these, chitin, or β-1,3-glucan, has been the main target for the development of antifungal agents. Chitin is a homopolymer constructed from units of N-acetyl-d-glucosamine linked with β-1,4 glycoside bond. It is an essential component in the cell walls of almost all pathogenic fungi and the skeletal structures of in-vertebrates. Chitin is synthesized by chitin synthases 1, 2 and 3. Like *Saccharomyces cerevisiae, Candida albicans* harbours three chitin synthases 1, 2 and 3, which are analogous in terms of structure and function to those of *Saccharomyces cerevisiae* chitin synthases 2, 1 and 3, respectively. Chitin synthase 1 from *Candida albicans* participates in septum formation during cell division, while chitin synthase 3 participates in chitin ring formation during the formation of daughter cells from mother cells and the cell wall biogenesis. On the other hand, chitin synthase 2 recovers severely damaged cell wall during cell division (Mio T. et al., *J. Bacteriol.,* 178, 2416-2419, 1996). Among them, chitin synthases 1 and 3 are the main targets for the development of new cell wall biogenesis inhibitors, as they are known as essential enzymes.

Berberine, the main component of *Coptis chinensis* Fr., which has been known as Huang Lian in Oriental medicine and has been used for the treatment for eye disease, diarrhea or inflammation, is gaining attention because of its antifungal activity. Many researches on berberine derivatives have been reported.

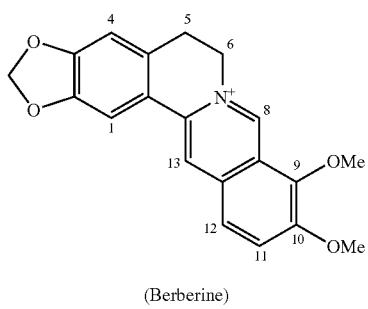

(Berberine)

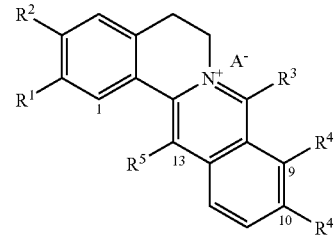

Particularly, berberine derivatives with a variety of functional groups substituted at the C-13 position have chitin synthase inhibitory effect and antifungal activity (Korean Patent No. 258849; Park K. S., et al., *J. Antimicrob. Chemother.*, 47, 513, 2001).

The compound obtained by pyrolyzing berberine at high temperature to replace the methoxy group at the C-9 position with a hydroxyl group is called berberrubine. As shown below, the hydroxyl group at the C-9 position of berberrubine is present in the form of either a ketone group or a hydroxyl group and is reversibly transformed, as shown in the following formula:

However, according to the experiments carried out by the present inventors, the berberrubine derivatives of the present invention, in which methoxy is present at the C-10 position and a variety of $C_3$-$C_{10}$ alkoxy are substituted at the C-9 position, showed more potent antifungal activities than those of the substituted berberine derivatives of Korean Patent No. 258,849, in which identical substituents (methoxy) are substituted at the C-9 and C-10 positions (see Table 3 and Table 4 below). For the synthesis of the berberrubine derivatives introduced alkoxy groups at the C-9 position only, berberrubine used as a intermediate was synthesized by pyrolysis.

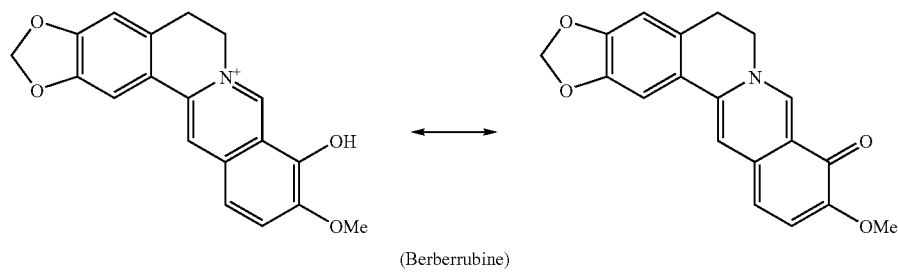

(Berberrubine)

Recently, a berberrubine derivative having improved antifungal activity or DNA-binding affinity by introducing an acyl or alkyl chain at the hydroxyl group of the C-9 position was reported (Kim S. H., Lee S. J., Lee J. Y., Sun W. S., Kim J. H., *Planta Medica* 03, 277(2002); Pang J. Y., Qin Y., Chen W. H., Luo G. A., Jiang Z. H., *Bioorganic & Medicinal Chemistry* 13, 5835(2005)). However, the introduction was restricted to the hydroxyl group at the C-9 position of berberrubine and a good antifungal activity was attained only when a hydrocarbon chain longer than 8 carbon atoms was introduced, yet it did not have chitin synthase inhibitory effect. Thus, the antifungal activity could be due to the destruction of cell membrane by the long hydrocarbon chain, and not due to the inhibition of chitin synthase. Such a long hydrocarbon chain renders the development difficult because of its intrinsic toxicity and low hydrophilicity as hydrocarbon.

Korean Patent No. 258,849 discloses that berberine derivatives in which various benzyl groups are introduced at the C-13 position or at the same time alkoxy groups are introduced at the C-9 and C-10 positions instead of two methoxy groups. In practice, only the berberine derivative represented by the following formula, wherein $R^1$ and $R^2$ are —O—$CH_2$—O— or $OCH_3$, $R^3$ is H, $R^4$ is $OCH_3$ and $R^5$ is benzyl or substituted benzyl, is known to have antifungal activity.

DISCLOSURE

The present inventors worked to synthesize new berberrubine derivatives that can solve the problems of the existing antifungal agents, have selective inhibitory effect against chitin synthase, that are absent in mammals, and have superior antifungal activity.

As a result, they synthesized berberrubine derivatives having a novel structure, in which a variety of functional groups are introduced at the C-9 and C-13 position positions of berberrubine, and confirmed that these compounds have superior inhibitory activities against chitin synthase and antifungal activities against human pathogenic fungi. In particular, the berberrubine derivatives of the present invention in which both the C-9 and C-13 positions are substituted by functional groups were confirmed to have more than 5 times of inhibitory activities against chitin synthase and over 16 to 25 times of antifungal activities, when compared with those of the conventional berberine derivatives or berberrubine derivatives.

With improved cell permeability, the novel compounds of the present invention effectively inhibit chitin synthases, and thus have very potent antifungal activity against human pathogenic fungi such as *Candida albicans* ATCC 10231, *Candida lusitaniae* ATCC 42720, *Candida krusei* ATCC 6258, *Candida tropicalis* ATCC 13803, *Candida glabrata* ATCC 48435, *Candida parapsilosis* ATCC 34136, *Cryptococcus neoformans ATCC 36556, *Aspergillus fumigatus* ATCC 16424, *Aspergillus flavus* ATCC 64025, *Aspergillus terreus* ATCC 46941, *Mucor ramosissimus* ATCC 90286, *Candida albicans* A207(clinical isolate), *Trichophyton mentagrophytes* ATCC 9533, etc.

Thus, it is an object of the present invention to provide a novel berberrubine derivative having superior antifungal activity.

It is yet another object of the present invention to provide an antifungal agent having superior inhibitory activity against chitin biogenesis of fungi and potent antifungal activity against human pathogenic fungi, which comprises the berberrubine derivative or a pharmaceutically acceptable salt thereof as an active ingredient.

The present invention is characterized by a berberrubine derivative represented by the following formula (1) or a pharmaceutically acceptable salt thereof:

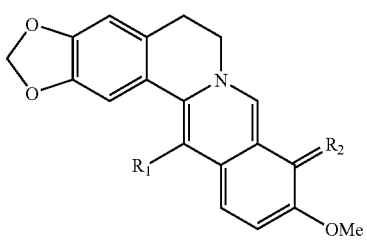

(1)

wherein $R_1$ is benzyl or substituted benzyl; $R_2$ is ketone (=O) or OR, wherein R is $C_3$-$C_{10}$ alkyl, $C_1$-$C_{10}$ haloalkyl, $C_1$-$C_{10}$ hydroxyalkyl, $C_2$-$C_{10}$ alkenyl, benzyl or substituted benzyl; and the substituted benzyl is a substituted benzyl having 1 to 4 substituents selected from halogen atom, $C_1$-$C_6$ alkyl, $C_1$-$C_6$ haloalkyl, $C_1$-$C_6$ alkoxy, and $C_1$-$C_6$ haloalkoxy.

The present invention is also characterized by an antifungal agent which comprises the berberrubine derivative represented by the aforementioned formula (1) or a pharmaceutically acceptable salt thereof as an active ingredient.

Hereunder is given a more detailed description of the present invention.

The compound of the present invention which is represented by the aforementioned formula (1) can be used in the form of a pharmaceutically acceptable salt, which may be a halide or an acid adduct. More specifically, the pharmaceutically acceptable salt of the compound represented by the aforementioned formula (1) may be selected from fluoride, chloride, bromide, iodide, hydroxide, nitrate, sulfate, acetate, phosphate, tartarate, succinate, lactate, citrate, fumarate, maleate, glycolate, formate, malate, benzoate, methanesulfonate, benzenesulfonate, asparaginate, salicylate, glycerate and ascorbinate.

Also, the compound of the present invention which is represented by the aforementioned formula (1) may be in the form of solvate (e.g., hydrate).

Preferably, in the compound of the present invention which is represented by the formula (1), $R_1$ is benzyl or substituted benzyl having 1 to 4 substituents selected from halogen, $C_1$-$C_6$ alkyl, $C_1$-$C_6$ haloalkyl, $C_1$-$C_6$ alkoxy and $C_1$-$C_6$ haloalkoxy and $R_2$ is ketone (=O) or OR, wherein R is $C_6$-$C_{10}$ alkyl, $C_1$-$C_6$ haloalkyl, $C_1$-$C_6$ hydroxyalkyl, $C_2$-$C_6$ alkenyl, benzyl or $C_1$-$C_6$ alkyl substituted benzyl.

Examples of the particularly preferable compound of the present invention which is represented by the formula (1) are as follows:

13-(3,4,5-trifluorobenzyl)berberrubine (Compound No. 1),
13-(3,4,5-trimethoxybenzyl)berberrubine (Compound No. 2),
13-(4-trifluoromethoxybenzyl)berberrubine (Compound No. 3),
13-(4-trifluoromethylbenzyl)berberrubine (Compound No. 4),
13-(4-tert-butylbenzyl)berberrubine (Compound No. 5),
13-(4-isopropylbenzyl)berberrubine (Compound No. 6),
13-(4-tert-butylbenzyl)-9-O-propylberberrubine iodide (Compound No. 7),
13-(4-tert-butylbenzyl)-9-O-butylberberrubine iodide (Compound No. 8),
13-(4-tert-butylbenzyl)-9-O-hexylberberrubine iodide (Compound No. 9),
13-(4-tert-butylbenzyl)-9-O-octylberberrubine iodide (Compound No. 10),
13-(4-tert-butylbenzyl)-9-O-(3-hydroxypropyl)berberrubine iodide (Compound No. 11),
13-(4-tert-butylbenzyl)-9-O-(6-chlorohexyl)berberrubine iodide (Compound No. 12),
13-(4-tert-butylbenzyl)-9-O-allylberberrubine iodide (Compound No. 13),
13-(4-tert-butylbenzyl)-9-O-crotylberberrubine bromide (Compound No. 14),
13-(4-tert-butylbenzyl)-9-O-(4-tert-butylbenzyl)berberrubine bromide (Compound No. 15),
13-(4-tert-butylbenzyl)-9-O-(4-isopropylbenzyl)berberrubine bromide (Compound No. 16),
13-(4-isopropylbenzyl)-9-O-propylberberrubine iodide (Compound No. 17),
13-(4-isopropylbenzyl)-9-O-butylberberrubine iodide (Compound No. 18),
13-(4-isopropylbenzyl)-9-O-hexylberberrubine iodide (Compound No. 19),
13-(4-isopropylbenzyl)-9-O-octylberberrubine iodide (Compound No. 20),
13-(4-isopropylbenzyl)-9-O-(3-hydroxypropyl)berberrubine iodide (Compound No. 21),
13-(4-isopropylbenzyl)-9-O-(6-chlorohexyl)berberrubine iodide (Compound No. 22),
13-(4-isopropylbenzyl)-9-O-allylberberrubine iodide (Compound No. 23),
13-(4-isopropylbenzyl)-9-O-crotylberberrubine bromide (Compound No. 24),
13-(4-isopropylbenzyl)-9-O-(4-tert-butylbenzyl)berberrubine bromide (Compound No. 25),
13-(4-isopropylbenzyl)-9-O-(4-isopropylbenzyl)berbembine bromide (Compound No. 26),
13-(3,4,5-trifluorobenzyl)-9-O-butylberberrubine iodide (Compound No. 27),
13-(3,4,5-trifluorobenzyl)-9-O-hexylberberrubine iodide (Compound No. 28),
13-(3,4,5-trifluorobenzyl)-9-O-(4-tert-butylbenzyl)berberrubine bromide (Compound No. 29),
13-(3,4,5-trimethoxybenzyl)-9-O-butylberberrubine iodide (Compound No. 30),
13-(3,4,5-trimethoxybenzyl)-9-O-hexylberberrubine iodide (Compound No. 31),
13-(3,4,5-trimethoxybenzyl)-9-O-(4-tert-butylbenzyl) berberrubine bromide (Compound No. 32),
13-(4-trifluoromethoxybenzyl)-9-O-butylberberrubine iodide (Compound No. 33),
13-(4-trifluoromethoxybenzyl)-9-O-hexylberberrubine iodide (Compound No. 34), 13-(4-trifluoromethoxybenzyl)-9-O-(4-tert-butylbenzyl) berberrubine bromide (Compound No. 35), 13-(4-trifluoromethylbenzyl)-9-O-butylberberrubine iodide (Compound No. 36), 13-(4-trifluoromethylbenzyl)-9-O-hexylberberrubine iodide (Compound No. 37), 13-(4-trifluoromethylbenzyl)-9-O-(4-tert-butylbenzyl) berberrubine bromide (Compound No. 38), 13-(4-tert-butylbenzyl)-9-O-propylberberrubine chloride (Compound No. 39), 13-(4-tert-butylbenzyl)-9-O-butylberberrubine chloride (Compound No. 40), 13-(4-tert-butylbenzyl)-9-O-hexylberberrubine chloride (Compound No. 41), 13-(4-tert-butylbenzyl)-9-O-octylberberrubine chloride (Compound No. 42), 13-(4-tert-butylbenzyl)-9-O-(3-hydroxypropyl)berberrubine chloride (Compound No. 43), 13-(4-tert-butylbenzyl)-9-O-(6-chlorohexyl)berberrubine chloride (Compound No. 44), 13-(4-tert-butylbenzyl)-9-O-allylberberrubine chloride (Compound No. 45), 13-(4-tert-butylbenzyl)-9-O-crotylberberrubine chloride (Compound No. 46), 13-(4-tert-butylbenzyl)-9-O-(4-tert-butylbenzyl)berberrubine chloride (Compound No. 47), 13-(4-tert-butylbenzyl)-9-O-(4-isopropylbenzyl)berberrubine chloride (Compound No. 48), 13-(4-isopropylbenzyl)-9-O-propylberberrubine chloride (Compound No. 49), 13-(4-isopropylbenzyl)-9-O-butylberberrubine chloride (Compound No. 50), 13-(4-isopropylbenzyl)-9-O-hexylberberrubine chloride (Compound No. 51), 13-(4-isopropylbenzyl)-9-O-octylberberrubine chloride (Compound No. 52), 13-(4-isopropylbenzyl)-9-O-(3-hydroxypropyl)berberrubine chloride (Compound No. 53), 13-(4-isopropylbenzyl)-9-O-(6-chlorohexyl)berberrubine chloride (Compound No. 54), 13-(4-isopropylbenzyl)-9-O-allylberberrubine chloride (Compound No. 55), 13-(4-isopropylbenzyl)-9-O-crotylberberrubine chloride (Compound No. 56), 13-(4-isopropylbenzyl)-9-O-(4-tert-butylbenzyl)berberrubine chloride (Compound No. 57), 13-(4-isopropylbenzyl)-9-O-(4-isopropylbenzyl)berberrubine chloride (Compound No. 58), 13-(3,4,5-trifluorobenzyl)-9-O-butylberberrubine chloride (Compound No. 59), 13-(3,4,5-trifluorobenzyl)-9-O-hexylberberrubine chloride (Compound No. 60), 13-(3,4,5-trifluorobenzyl)-9-O-(4-tert-butylbenzyl)berberrubine chloride (Compound No. 61), 13-(3,4,5-trimethoxybenzyl)-9-O-butylberberrubine chloride (Compound No. 62), 13-(3,4,5-trimethoxybenzyl)-9-O-hexylberberrubine chloride (Compound No. 63), 13-(3,4,5-trimethoxybenzyl)-9-O-(4-tert-butylbenzyl) berberrubine chloride (Compound No. 64), 13-(4-trifluoromethoxybenzyl)-9-O-butylberberrubine chloride (Compound No. 65), 13-(4-trifluoromethoxybenzyl)-9-O-hexylberberrubine chloride (Compound No. 66), 13-(4-trifluoromethoxybenzyl)-9-O-(4-tert-butylbenzyl) berberrubine chloride (Compound No. 67), 13-(4-trifluoromethylbenzyl)-9-O-butylberberrubine chloride (Compound No. 68), 13-(4-trifluoromethylbenzyl)-9-O-hexylberberrubine chloride (Compound No. 69), 13-(4-trifluoromethylbenzyl)-9-O-(4-tert-butylbenzyl) berberrubine chloride (Compound No. 70) and pharmaceutically acceptable salts thereof.

The novel compound in accordance with the present invention has superior inhibitory activity against chitin synthase (chitin synthase 1), which participates in chitin biogenesis, and potent antifungal activity against human pathogenic fungi. The present invention also provides a pharmaceutical composition comprising the compound represented by the aforementioned formula (1) or a pharmaceutically acceptable salt thereof as an active ingredient.

The pharmaceutical composition of the present invention comprises the compound represented by the aforementioned formula (1) or a pharmaceutically acceptable salt thereof as an active ingredient and a pharmaceutically acceptable excipient.

The pharmaceutical composition of the present invention may be prepared into: oral administration form including tablet, capsule and syrup; injection form; suppository form; external application form including ointment, cream, lotion and liquid; etc.

The present invention also provides a method for the prevention and the treatment of systemic infection by fungi in mammals by administering an effective dosage of the compound, represented by the aforementioned formula (1) or a pharmaceutically acceptable salt thereof.

The compound of the present invention can be orally administered in the form of a tablet, a capsule (sustained release or controlled release), a pill, powder, a granule, an elixir, a tincture, a suspension, a syrup or an emulsion. Also, it can be administered by the method well known by those skilled in the art, e.g., intravenously, intraperitoneally, locally (e.g., eye drops), subcutaneously, intramuscularly, transdermally (e.g., patches), etc.

The dosage of the compound of the present invention is determined by considering age, weight, sex, physical conditions, etc. of a patient, seriousness of the conditions to be treated, administration route, liver or lung function of the patient, the particular compound or the salt to be used, etc. An average doctor, veterinarian or clinician may easily determine the pharmaceutically effective dosage required for the prevention or inhibition of the development of the condition.

The oral dosage for attaining the purpose of the present invention is about 0.01-100 mg/kg/day, preferably about 0.01-10 mg/kg/day, and more preferably about 0.1-5.0 mg/kg/day. For oral administration, it is preferable that the composition is provided in the form of tablet comprising the active ingredient in 0.01, 0.05, 0.1, 0.5, 1.0, 2.5, 5.0, 10.0, 15.0, 25.0, 50.0, 100 and 500 mg in order to find the adequate dosage for the particular patient. Typically, a drug comprises the active ingredient in the range from about 0.01 mg to about 500 mg, preferably from about 1 mg to about 100 mg. In case of an intravenous injection, the most preferred dosage is 0.1-10 mg/kg/min. The compound of the present invention may be administered once, twice, three times or four times daily. Also, preferably, the compound of the present invention may be administered either intranasally using an adequate intranasal carrier or transdermally using a commonly used transdermal patch. It is obvious that the transdermal administration ensures a continuous administration.

The compound of the present invention, or the active ingredient, may be mixed with a pharmaceutically acceptable diluent or excipient (collectively, the 'excipient'), which is selected considering the type of administration.

For example, in case of oral administration using tablet or capsule, the active ingredient may be mixed with non-toxic, pharmaceutically acceptable excipient, such as lactose, starch, sucrose, glucose, methylcellulose, magnesium stearate, calcium phosphate dibasic, calcium sulfate, mannitol, sorbitol, etc. In case of liquid type oral administration, the active ingredient may be mixed with non-toxic, pharmaceutically acceptable excipient such as ethanol, glycerol, water, etc. If required, an adequate binder, lubricant, dispersant or colorant may be added to the mixture solution. The binder may be natural sugars such as starch, gelatin, glucose and β-lactose, natural or synthetic rubbers such as corn sweetener, acacia and sodium alginate, carboxymethyl-cellulose, polyethylene glycol, wax, etc. The lubricant may be sodium oleate, sodium stearate, magnesium stearate, sodium benzoate, sodium acetate, sodium chloride, etc. And, the dispersant may be starch, methylcellulose, agar, bentonite, xanthan rubber, etc.

The method for preparing the novel compound of the present invention represented by the aforementioned formula (1) can be schematically illustrated by the following Scheme 1.

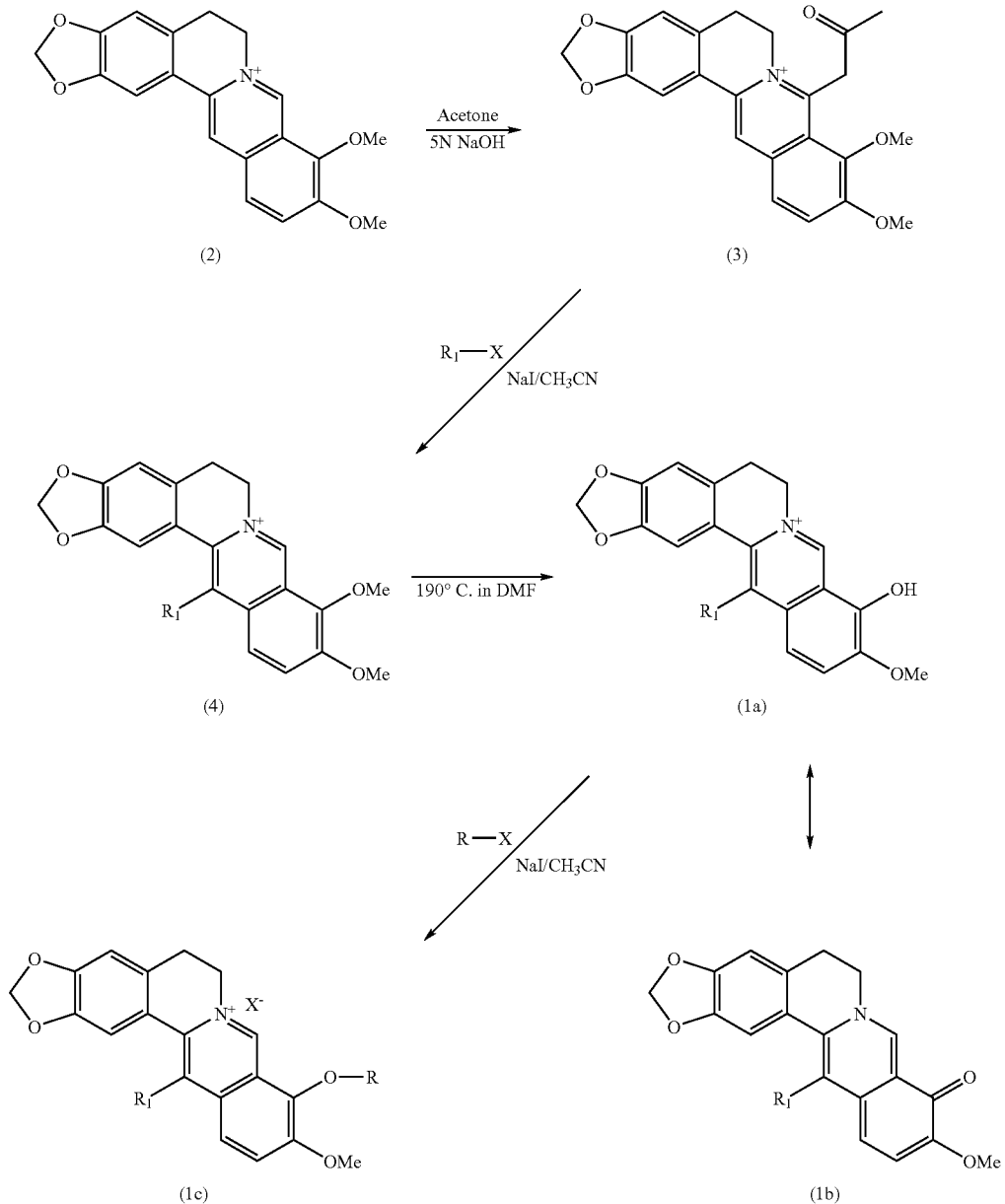

In Scheme 1, R and $R_1$ are the same as defined above, $X^-$ is a halide ion or an acid anion derived from an organic or inorganic acid.

First, an acetonyl group is introduced at the C-8 position of the berberine salt represented by the aforementioned formula (2) to obtain the 8-acetonyldihydroberberine represented by the aforementioned formula (3). Then, an electrophilic alkyl substituent ($R_1$—X, where X is a halogen atom) is used to synthesize the compound represented by the aforementioned formula (4), wherein the functional group $R_1$ is introduced at the C-13 position. The resultant compound represented by the aforementioned formula (4) is pyrolyzed at high temperature to obtain the berberrubine derivative represented by the aforementioned formula (1a), wherein a hydroxyl group is introduced at the C-9 position. The resultant berberrubine derivative represented by the aforementioned formula (1a) is reversibly converted to the berberrubine derivative represented by the aforementioned formula (1b), wherein a ketone (O=) is introduced at the C-9 position. Furthermore, in order to introduce various functional groups R at the C-9 position, an electrophilic alkyl substituent (R—X, where X is halogen atom) is reacted with the compound represented by the formula (1a) or (1b) to attain the novel compound represented by the aforementioned formula (1c), wherein both C-9 and C-13 positions are substituted by the functional groups.

In Scheme 1, the introduction of the acetonyl group at the C-8 position of the berberine salt represented by the aforementioned formula (2) is carried out using acetone and, if necessary, a suitable organic solvent and a commonly used organic or inorganic base may be added.

And, the introduction of the functional group at the C-13 position of the 8-acetonyldihydroberberine represented by the aforementioned formula (3) and the introduction of the functional group R at the C-9 position of the berberrubine derivative represented by the aforementioned formula (1a) are carried out, respectively, using an adequate electrophilic alkyl substituent. During the reaction with the electrophilic alkyl substituent, a suitable organic solvent and a commonly used organic or inorganic base may be added, if necessary.

And, the pyrolysis of the compound represented by the aforementioned formula (4) for substituting the methoxy group at the C-9 position with the hydroxyl group is performed at 170-190° C.

In the preparation in accordance with the present invention, a commonly used organic solvent selected from methylene chloride, chloroform, acetonitrile, dimethylformamide, tetrahydrofuran, etc., may be used as the reaction solvent. For the base, organic bases such as amine or inorganic bases such as alkali metal hydride, hydroxide, carbonate, etc., may be used. Specifically, the base may be selected from ammonia, triethylamine, sodium hydride, potassium hydride, lithium hydride, potassium carbonate, or sodium carbonate, etc.

The reaction intermediate or the target compound represented by the aforementioned formula (1) obtained by the preparation process may be separated and purified by the commonly utilized method, such as chromatography and recrystallization.

BEST MODE

Practical and preferred embodiments of the present invention are illustrated as shown in the following examples. However, it will be appreciated that those skilled in the art may, in consideration of this disclosure, make modifications and improvements within the spirit and scope of the present invention.

EXAMPLE 1

13-(3,4,5-Trifluorobenzyl)berberrubine (Compound No. 1)

55 mL of 5 N NaOH solution was added to 10 g of berberine chloride. 8 mL of acetone was slowly added while vigorously stirring the solution. The reaction was performed at room temperature for 1 hour. The reaction solution was filtered, sufficiently washed with 80% methanol and dried to obtain 9.2 g of 8-acetonyldihydroberberine. 1.8 g of 8-acetonyldihydroberberine was dissolved in 60 mL of acetonitrile ($CH_3CN$). Then, 0.42 g of sodium iodide (NaI) and 1.4 mL of 3,4,5-trifluorobenzyl bromide were added and the reaction was performed at 80° C. for 4 hours. The reaction solution was concentrated under reduced pressure and then washed with ethyl ether. 1.1 g of 13-(3,4,5-trifluoro)berberine was obtained from silica gel column chromatography. During the chromatography, a 1:20 organic solvent mixture of methanol and chloroform was used as an eluent.

1 g of 13-(3,4,5-trifluoro)berberine was dissolved in DMF. After vigorously stirring at 190° C. for 2 hours, the reaction solution was concentrated under reduced pressure. 0.56 g of 13-(3,4,5-trifluoro)berberrubine was obtained from chromatography using silica gel and a 1:9 solvent mixture of methanol and chloroform.

$^1$H-NMR (DMSO-$d_6$, 300 MHz) δ 9.42 (s, 1H), 7.61 (s, 1H), 7.31 (s, 1H), 7.12 (d, 1H), 6.79 (d, 2H), 6.24 (d, 1H), 5.98(s, 2H), 4.49 (s, 2H), 4.42 (broad s, 2H), 3.87 (s, 3H) 3.04 (t, 2H).

EXAMPLE 2

13-(3,4,5-Trimethoxybenzyl)berberrubine (Compound No. 2)

0.61 g of 13-(3,4,5-trimethoxybenzyl)berberrubine was obtained in the same manner as in the aforementioned Example 1, except that 3,4,5-trimethoxybenzyl bromide was used instead of 3,4,5-trifluorobenzyl bromide.

$^1$H-NMR (DMSO-$d_6$, 300 MHz) δ 9.46 (s, 1H), 7.63 (s, 1H), 7.32 (s, 1H), 7.13 (d, 1H), 6.77 (d, 2H), 6.22 (d, 1H), 5.99(s, 2H), 4.51 (s, 2H), 4.44 (broad s, 2H), 4.04 (s, 3H), 3.91 (s, 6H), 3.87 (s, 3H) 3.04 (t, 2H).

EXAMPLE 3

13-(4-Trifluoromethoxybenzyl)berberrubine (Compound No. 3)

0.48 g of 13-(4-trifluoromethoxybenzyl)berberrubine was obtained in the same manner as in the aforementioned Example 1, except that 4-trifluoromethoxybenzyl bromide was used instead of 3,4,5-trifluorobenzyl bromide.

$^1$H-NMR (DMSO-$d_6$, 300 MHz) δ: 9.48 (s, 1H), 7.45 (d, 1H), 7.31 (s, 1H), 7.18 (d, 1H), 7.08 (s, 1H), 7.06 (s, 1H), 6.87 (s, 1H), 6.85 (s, 1H), 6.46 (d, 1H), 5.97 (s, 2H), 4.43 (t, 2H), 4.41 (s, 2H), 3.89 (s, 3H) 3.02 (t, 2H).

EXAMPLE 4

13-(4-Trifluoromethylbenzyl)berberrubine (Compound No. 4)

0.43 g of 13-(4-trifluoromethylbenzyl)berberrubine was obtained in the same manner as in the aforementioned Example 1, except that 4-trifluoromethylbenzyl bromide was used instead of 3,4,5-trifluorobenzyl bromide.

$^1$H-NMR (DMSO-$d_6$, 300 MHz) δ 9.42 (s, 1H), 7.61 (s, 1H), 7.58 (s, 1H), 7.31 (s, 1H), 7.29 (s, 1H), 7.12 (d, 1H), 6.79 (d, 2H), 6.24 (d, 1H), 5.98 (s, 2H), 4.49 (s, 2H), 4.42 (broad s, 2H), 3.87 (s, 3H) 3.04 (t, 2H).

EXAMPLE 5

13-(4-tert-Butylbenzyl)berberrubine (Compound No. 5)

0.63 g of 13-(4-tert-butylbenzyl)berberrubine was obtained in the same manner as in the aforementioned Example 1, except that 4-tert-butylbenzyl bromide was used instead of 3,4,5-trifluorobenzyl bromide.

$^1$H-NMR (DMSO-$d_6$, 300 MHz) δ 9.5 (s, 1H), 7.34 (s, 1H), 7.31 (s, 1H), 7.18 (d, 1H), 7.08 (s, 1H), 7.06 (s, 1H), 6.98 (s, 1H), 6.78 (s, 1H), 6.43 (d, 1H), 5.97 (s, 2H), 4.42 (t, 2H), 4.40 (s, 2H), 3.88 (s, 3H) 3.03 (t, 2H) 1.31 (s, 9H).

EXAMPLE 6

13-(4-Isopropylbenzyl)berberrubine (Compound No. 6)

0.65 g of 13-(4-isopropylbenzyl)berberrubine was obtained in the same manner as in the aforementioned Example 1, except that 4-isopropylbenzyl bromide was used instead of 3,4,5-trifluorobenzyl bromide.

$^1$H-NMR (DMSO-$d_6$, 300 MHz) δ 9.51 (s, 1H), 7.35 (s, 1H), 7.34 (s, 1H), 7.16 (d, 1H), 7.06 (s, 1H), 7.02 (s, 1H), 6.97 (s, 1H), 6.76 (s, 1H), 6.41 (d, 1H), 5.98 (s, 2H), 4.44 (t, 2H), 4.42 (s, 2H), 3.87 (s, 3H) 3.05 (t, 2H) 2.82 (m, 1H), 1.33 (d, 6H).

EXAMPLE 7

13-(4-tert-Butylbenzyl)-9-O-propylberberrubine iodide (Compound No. 7)

0.5 g of 13-(4-tert-butylbenzyl)berberrubine obtained in the aforementioned Example 5 was dissolved in 50 mL of acetonitrile (CH$_3$CN). After completely dissolving the mixture by string at 120° C., a reaction was performed for 4 hours by slowly adding 0.25 mL of propyl iodide dropwise. The reaction solution was concentrated under reduced pressure. 0.32 g of 13-(4-tert-butylbenzyl)-9-O-propyl-berberrubine iodide was obtained from silica gel column chromatography (1:9/MeOH:CHCl$_3$).

$^1$H-NMR (DMSO-$d_6$, 300 MHz) δ 10.27 (s, 1H), 7.63 (m, 2H), 7.32 (d, 2H), 7.02 (s, 1H), 6.96 (s, 2H), 6.84 (s, 1H), 5.96 (s, 2H), 5.36 (broad t, 2H), 4.63 (s, 2H), 4.54 (t, 2H) 4.02 (s, 3H) 3.31 (t, 2H) 2.04 (m, 2H), 1.35 (s, 9H), 1.04 (t, 3H).

EXAMPLE 8

13-(4-tert-Butylbenzyl)-9-O-butylberberrubine iodide (Compound No. 8)

0.33 g of 13-(4-tert-butylbenzyl)-9-O-butylberberrubine iodide was obtained in the same manner as in the aforementioned Example 7, except that butyl iodide was used instead of propyl iodide.

$^1$H-NMR (DMSO-$d_6$, 300 MHz) δ 10.27 (s, 1H), 7.64 (m, 2H), 7.36 (d, 2H), 7.02 (s, 1H), 6.98 (s, 2H), 6.87 (s, 1H), 5.99 (s, 2H), 5.38 (broad t, 2H), 4.62 (s, 2H), 4.57 (t, 2H), 4.00 (s, 3H), 3.27 (t, 2H), 2.07 (m, 2H), 1.63 (m, 2H), 1.32 (s, 9H), 1.03 (t, 3H).

EXAMPLE 9

13-(4-tert-Butylbenzyl)-9-O-hexylberberrubine iodide (Compound No. 9)

0.35 g of 13-(4-tert-butylbenzyl)-9-O-hexylberberrubine iodide was obtained in the same manner as in the aforementioned Example 7, except that hexyl iodide was used instead of propyl iodide.

$^1$H-NMR (DMSO-$d_6$, 300 MHz) δ 10.31 (s, 1H), 7.67 (m, 2H), 7.38 (d, 2H), 7.04 (s, 1H), 6.93 (s, 2H), 6.86 (s, 1H), 5.97 (s, 2H), 5.34 (broad t, 2H), 4.65 (s, 2H), 4.56 (t, 2H), 4.02 (s, 3H), 3.24 (t, 2H), 2.04 (m, 2H), 1.43-1.79 (m, 6H), 1.31 (s, 9H), 1.05 (t, 3H).

EXAMPLE 10

13-(4-tert-Butylbenzyl)-9-O-octylberberrubine iodide (Compound No. 10)

0.32 g of 13-(4-tert-butylbenzyl)-9-O-octylberberrubine iodide was obtained in the same manner as in the aforementioned Example 7, except that octyl iodide was used instead of propyl iodide.

$^1$H-NMR (DMSO-$d_6$, 300 MHz) δ 10.28 (s, 1H), 7.69 (m, 2H), 7.40 (d, 2H), 7.07 (s, 1H), 6.95 (s, 2H), 6.88 (s, 1H), 5.98 (s, 2H), 5.35 (broad t, 2H), 4.64 (s, 2H), 4.54 (t, 2H) 4.04 (s, 3H) 3.25 (t, 2H) 2.06 (m, 2H), 1.44-1.80 (m, 10H), 1.33 (s, 9H), 1.03 (t, 3H).

EXAMPLE 11

13-(4-tert-Butylbenzyl)-9-O-(3-hydroxypropyl)berberrubine iodide (Compound No. 11)

0.23 g of 13-(4-tert-butylbenzyl)-9-O-(3-hydroxypropyl) berberrubine iodide was obtained in the same manner as in the aforementioned Example 7, except that 1-iodo-3-propanol was used instead of propyl iodide.

$^1$H-NMR (DMSO-$d_6$, 300 MHz) δ 10.56 (s, 1H), 7.65 (m, 2H), 7.37 (d, 2H), 7.03 (s, 1H), 7.00 (s, 2H), 6.87 (s, 1H), 6.00 (s, 2H), 5.20 (broad t, 2H), 4.69 (t, 2H), 4.63 (s, 2H), 4.05(t, 2H), 4.02 (s, 3H) 3.28 (t, 2H) 2.25 (m, 2H), 1.32 (s, 9H).

EXAMPLE 12

13-(4-tert-Butylbenzyl)-9-O-(6-chlorohexyl)berberrubine iodide (Compound No. 12)

0.27 g of 13-(4-tert-butylbenzyl)-9-O-(6-chlorohexyl)berberrubine iodide was obtained in the same manner as in the aforementioned Example 7, except that 1-chloro-6-iodohexane was used instead of propyl iodide.

$^1$H-NMR (DMSO-$d_6$, 300 MHz) δ 10.30 (s, 1H), 7.66 (m, 2H), 7.35 (d, 2H), 7.02 (d, 2H), 7.00 (s, 1H), 6.87 (s, 1H), 6.00 (s, 2H), 5.21 (broad t, 2H), 4.63 (s, 2H), 4.61 (t, 2H), 4.01 (s, 3H), 3.60 (t 2H), 3.30 (t, 2H) 2.10 (m, 2H), 1.89 (m, 2H), 1.58-1.64 (m, 4H), 1.32 (s, 9H).

EXAMPLE 13

13-(4-tert-Butylbenzyl)-9-O-allylberberrubine iodide (Compound No. 13)

0.24 g of 13-(4-tert-butylbenzyl)-9-O-allylberberrubine iodide was obtained in the same manner as in the aforementioned Example 7, except that allyl iodide was used instead of propyl iodide.

¹H-NMR (DMSO-d₆, 300 MHz) δ 10.55 (s, 1H), 7.65 (m, 2H), 7.36 (d, 2H), 7.03 (d, 2H), 6.99 (s, 1H), 6.87 (s, 1H), 6.49(m, 1H), 6.00 (s, 2H), 5.5 (dd, 1H), 5.33 (dd, 1H), 5.13 (d, 2H), 4.62 (s, 2H), 4.01 (s, 3H) 3.29 (t, 2H), 1.32 (s, 9H).

EXAMPLE 14

13-(4-tert-Butylbenzyl)-9-O-crotylberberrubine bromide (Compound No. 14)

0.22 g of 13-(4-tert-butylbenzyl)-9-O-crotylberberrubine bromide was obtained in the same manner as in the aforementioned Example 7, except that crotyl bromide was used instead of propyl iodide.
¹H-NMR (DMSO-d₆, 300 MHz) δ 10.52 (s, 1H), 7.64 (m, 2H), 7.36 (d, 2H), 7.02 (d, 2H), 6.99 (s, 1H), 6.87 (s, 1H), 6.12(m, 2H), 6.00 (s, 2H), 5.31 (broad, 2H), 5.06 (d, 2H), 4.62 (s, 2H), 4.01 (s, 3H) 3.30 (t, 2H), 1.77 (d, 3H), 1.32 (s, 9H).

EXAMPLE 15

13-(4-tert-Butylbenzyl)-9-O-(4-tert-butylbenzyl) berberrubine bromide (Compound No. 15)

0.38 g of 13-(4-tert-butylbenzyl)-9-O-(4-tert-butylbenzyl) berberrubine bromide was obtained in the same manner as in the aforementioned Example 7, except that 4-tert-butylbenzyl bromide was used instead of propyl iodide.
¹H-NMR (DMSO-d₆, 300 MHz) δ 10.34 (s, 1H), 7.77 (d, 2H), 7.66 (m, 2H), 7.36 (d, 2H), 7.27(s, 2H), 7.02 (d, 2H), 6.98 (s, 1H), 6.86 (s, 1H), 5.97 (s, 2H), 5.62 (s, 2H), 5.22 (broad t, 2H), 4.62 (s, 2H), 4.03 (s, 3H), 3.31 (t, 2H), 1.34 (s, 9H), 1.32 (s, 9H).

EXAMPLE 16

13-(4-tert-Butylbenzyl)-9-O-(4-isopropylbenzyl) berberrubine bromide (Compound No. 16)

0.34 g of 13-(4-tert-butylbenzyl)-9-O-(4-isopropylbenzyl) berberrubine bromide was obtained in the same manner as in the aforementioned Example 7, except that 4-isopropylbenzyl bromide was used instead of propyl iodide.
¹H-NMR (DMSO-d₆, 300 MHz) δ 10.38 (s, 1H), 7.77 (d, 2H), 7.67 (m, 2H), 7.36 (d, 2H), 7.28(s, 2H), 7.02 (d, 2H), 6.98 (s, 1H), 6.86 (s, 1H), 5.99 (s, 2H), 5.63 (s, 2H), 5.20 (broad t, 2H), 4.62 (s, 2H), 4.04 (s, 3H), 3.30 (t, 2H), 2.91 (m, 1H), 1.32 (s, 9H), 1.24 (d, 6H).

EXAMPLE 17

13-(4-Isopropylbenzyl)-9-O-propylberberrubine iodide (Compound No. 17)

0.5 g of 13-(4-isopropylbenzyl)berberrubine obtained in the aforementioned Example 6 was dissolved in 50 mL of acetonitrile (CH₃CN). After completely dissolving the mixture by string at 120° C., a reaction was performed for 4 hours by slowly adding 0.25 mL of propyl iodide dropwise. The reaction solution was concentrated under reduced pressure. 0.33 g of 13-(4-isopropylbenzyl)-9-O-propylberberrubine iodide was obtained from silica gel column chromatography (1:9/MeOH:CHCl₃).
¹H-NMR (DMSO-d₆, 300 MHz) δ 10.26 (s, 1H), 7.64 (m, 2H), 7.36 (d, 2H), 7.01 (s, 1H), 6.96 (s, 2H), 6.83 (s, 1H), 5.96 (s, 2H), 5.32 (broad t, 2H), 4.64 (s, 2H), 4.53 (t, 2H), 4.02 (s, 3H), 3.32 (t, 2H), 2.91 (m, 1H), 2.04 (m, 2H), 1.25 (d, 6H), 1.04 (t, 3H).

EXAMPLE 18

13-(4-Isopropylbenzyl)-9-O-butylberberrubine iodide (Compound No. 18)

0.31 g of 13-(4-isopropylbenzyl)-9-O-butylberberrubine iodide was obtained in the same manner as in the aforementioned Example 17, except that butyl iodide was used instead of propyl iodide.
¹H-NMR (DMSO-d₆, 300 MHz) δ 10.31 (s, 1H), 7.63 (m, 2H), 7.36 (d, 2H), 7.02 (s, 1H), 6.98 (s, 2H), 6.87 (s, 1H), 5.99 (s, 2H), 5.38 (broad t, 2H), 4.64 (s, 2H), 4.52 (t, 2H), 4.00 (s, 3H), 3.27 (t, 2H), 2.91 (m, 1H), 2.07 (m, 2H), 1.63 (m, 2H), 1.26 (d, 6H), 1.04 (t, 3H).

EXAMPLE 19

13-(4-Isopropylbenzyl)-9-O-hexylberberrubine iodide (Compound No. 19)

0.32 g of 13-(4-isopropylbenzyl)-9-O-hexylberberrubine iodide was obtained in the same manner as in the aforementioned Example 17, except that hexyl iodide was used instead of propyl iodide.
¹H-NMR (DMSO-d₆, 300 MHz) δ 10.32 (s, 1H), 7.67 (m, 2H), 7.36 (d, 2H), 7.02 (s, 1H), 6.93 (s, 2H), 6.86 (s, 1H), 5.97 (s, 2H), 5.34 (broad t, 2H), 4.65 (s, 2H), 4.56 (t, 2H), 4.02 (s, 3H), 3.24 (t, 2H), 2.91 (m, 1H), 2.04 (m, 2H), 1.43-1.78 (m, 6H), 1.25 (d, 6H), 1.05 (t, 3H).

EXAMPLE 20

13-(4-Isopropylbenzyl)-9-O-octylberberrubine iodide (Compound No. 20)

0.32 g of 13-(4-isopropylbenzyl)-9-O-octylberberrubine iodide was obtained in the same manner as in the aforementioned Example 17, except that octyl iodide was used instead of propyl iodide.
¹H-NMR (DMSO-d₆, 300 MHz) δ 10.28 (s, 1H), 7.69 (m, 2H), 7.40 (d, 2H), 7.07 (s, 1H), 6.95 (s, 2H), 6.88 (s, 1H), 5.98 (s, 2H), 5.35 (broad t, 2H), 4.64 (s, 2H), 4.54 (t, 2H) 4.04 (s, 3H) 3.25 (t, 2H) 2.92 (m, 1H), 2.06 (m, 2H), 1.44-1.81 (m, 10H), 1.27 (d, 6H), 1.03 (t, 3H).

EXAMPLE 21

13-(4-Isopropylbenzyl)-9-O-(3-hydroxypropyl)berberrubine iodide (Compound No. 21)

0.25 g of 13-(4-isopropylbenzyl)-9-O-(3-hydroxypropyl) berberrubine iodide was obtained in the same manner as in the aforementioned Example 17, except that 1-iodo-3-propanol was used instead of propyl iodide.
¹H-NMR (DMSO-d₆, 300 MHz) δ 10.26 (s, 1H), 7.65 (m, 2H), 7.37 (d, 2H), 7.03 (s, 1H), 7.00 (s, 2H), 6.87 (s, 1H), 6.00 (s, 2H), 5.20 (broad t, 2H), 4.69 (t, 2H), 4.63 (s, 2H), 2H), 4.02 (s, 3H), 3.28 (t, 2H), 2.90 (m, 1H), 2.25 (m, 2H), 1.27 (d, 6H).

EXAMPLE 22

13-(4-Isopropylbenzyl)-9-O-(6-chlorohexyl)berberrubine iodide (Compound No. 22)

0.29 g of 13-(4-isopropylbenzyl)-9-O-(6-chlorohexyl)berberrubine iodide was obtained in the same manner as in the aforementioned Example 17, except that 1-chloro-6-iodohexane was used instead of propyl iodide.

$^1$H-NMR (DMSO-d$_6$, 300 MHz) δ 10.30 (s, 1H), 7.66 (m, 2H), 7.35 (d, 2H), 7.02 (d, 2H), 7.00 (s, 1H), 6.87 (s, 1H), 6.00 (s, 2H), 5.21 (broad t, 2H), 4.63 (s, 2H), 4.61 (t, 2H), 4.01 (s, 3H), 3.60 (t 2H), 3.30 (t, 2H), 2.91 (m, 1H), 2.10 (m, 2H), 1.89 (m, 2H), 1.58-1.64 (m, 4H), 1.28 (d, 6H).

EXAMPLE 23

13-(4-Isopropylbenzyl)-9-O-allylberberrubine iodide (Compound No. 23)

0.26 g of 13-(4-isopropylbenzyl)-9-O-allylberberrubine iodide was obtained in the same manner as in the aforementioned Example 17, except that allyl iodide was used instead of propyl iodide.

$^1$H-NMR (DMSO-d$_6$, 300 MHz) δ 10.25 (s, 1H), 7.65 (m, 2H), 7.36 (d, 2H), 7.03 (d, 2H), 6.99 (s, 1H), 6.87 (s, 1H), 6.49(m, 1H), 6.00 (s, 2H), 5.5 (dd, 1H), 5.33 (dd, 1H), 5.13 (d, 2H), 4.62 (s, 2H), 4.01 (s, 3H) 3.29 (t, 2H), 2.92 (m, 1H), 1.26 (d, 6H).

EXAMPLE 24

13-(4-Isopropylbenzyl)-9-O-crotylberberrubine bromide (Compound No. 24)

0.25 g of 13-(4-isopropylbenzyl)-9-O-crotylberberrubine bromide was obtained in the same manner as in the aforementioned Example 17, except that crotyl bromide was used instead of propyl iodide.

$^1$H-NMR (DMSO-d$_6$, 300 MHz) δ 10.30 (s, 1H), 7.64 (m, 2H), 7.36 (d, 2H), 7.02 (d, 2H), 6.99 (s, 1H), 6.87 (s, 1H), 6.12(m, 2H), 6.00 (s, 2H), 5.31 (broad, 2H), 5.06 (d, 2H), 4.62 (s, 2H), 4.01 (s, 3H) 3.30 (t, 2H), 2.91 (m, 1H), 1.77 (d, 3H), 1.26 (d, 6H).

EXAMPLE 25

13-(4-Isopropylbenzyl)-9-O-(4-tert-butylbenzyl) berberrubine bromide (Compound No. 25)

0.37 g of 13-(4-isopropylbenzyl)-9-O-(4-tert-butylbenzyl) berberrubine bromide was obtained in the same manner as in the aforementioned Example 17, except that 4-tert-butylbenzyl bromide was used instead of propyl iodide.

$^1$H-NMR (DMSO-d$_6$, 300 MHz) δ 10.34 (s, 1H), 7.77 (d, 2H), 7.66 (m, 2H), 7.36 (d, 2H), 7.27(s, 2H), 7.02 (d, 2H), 6.98 (s, 1H), 6.86 (s, 1H), 5.97 (s, 2H), 5.62 (s, 2H), 5.22 (broad t, 2H), 4.62 (s, 2H), 4.03 (s, 3H), 3.31 (t, 2H), 2.91 (m, 1H), 1.32 (s, 9H), 1.26 (d, 6H).

EXAMPLE 26

13-(4-Isopropylbenzyl)-9-O-(4-isopropylbenzyl) berberrubine bromide (Compound No. 26)

0.36 g of 13-(4-isopropylbenzyl)-9-O-(4-isopropylbenzyl) berberrubine bromide was obtained in the same manner as in the aforementioned Example 17, except that 4-isopropylbenzyl bromide was used instead of propyl iodide.

$^1$H-NMR (DMSO-d$_6$, 300 MHz) δ 10.31 (s, 1H), 7.78 (d, 2H), 7.67 (m, 2H), 7.36 (d, 2H), 7.28(s, 2H), 7.02 (d, 2H), 6.98 (s, 1H), 6.85 (s, 1H), 5.99 (s, 2H), 5.63 (s, 2H), 5.20 (broad t, 2H), 4.62 (s, 2H), 4.04 (s, 3H), 3.30 (t, 2H) 2.91 (m, 2H), 1.27 (d, 6H), 1.24 (d, 6H).

EXAMPLE 27

13-(3,4,5-Trifluorobenzyl)-9-O-butylberberrubine iodide (Compound No. 27)

0.2 g of 13-(3,4,5-trifluorobenzyl)berberrubine obtained in the aforementioned Example 1 was dissolved in 50 mL of acetonitrile (CH$_3$CN). After completely dissolving the mixture by string at 120° C., a reaction was performed for 4 hours by slowly adding 0.1 mL of butyl iodide dropwise. The reaction solution was concentrated under reduced pressure. 0.08 g of 13-(3,4,5-trifluorobenzyl)-9-O-butylberberrubine iodide was obtained from silica gel column chromatography (1:9/ MeOH:CHCl$_3$).

$^1$H-NMR (DMSO-d$_6$, 300 MHz) δ 10.26 (s, 1H), 7.64 (s, 1H), 7.36 (s, 1H), 7.01 (s, 1H), 6.96 (s, 2H), 6.83 (s, 1H), 5.96 (s, 2H), 5.34 (broad t, 2H), 4.63 (s, 2H), 4.52 (t, 2H), 4.01 (s, 3H), 3.33 (t, 2H), 2.07 (m, 2H), 1.63 (m, 2H), 1.04 (t, 3H).

EXAMPLE 28

13-(3,4,5-Trifluorobenzyl)-9-O-hexylberberrubine iodide (Compound No. 28)

0.09 g of 13-(3,4,5-trifluorobenzyl)-9-O-hexylberberrubine iodide was obtained in the same manner as in the aforementioned Example 27, except that hexyl iodide was used instead of butyl iodide.

$^1$H-NMR (DMSO-d$_6$, 300 MHz) δ 10.32 (s, 1H), 7.62 (s, 1H), 7.34 (s, 1H), 7.01 (s, 1H), 6.93 (s, 2H), 6.86 (s, 1H), 5.97 (s, 2H), 5.34 (broad t, 2H), 4.65 (s, 2H), 4.56 (t, 2H), 4.02 (s, 3H), 3.24 (t, 2H), 2.04 (m, 2H), 1.43-1.78 (m, 6H), 1.05 (t, 3H).

EXAMPLE 29

13-(3,4,5-Trifluorobenzyl)-9-O-(4-tert-butylbenzyl) berberrubine bromide (Compound No. 29)

0.1 g of 13-(3,4,5-trifluorobenzyl)-9-O-(4-tert-butylbenzyl)berberrubine bromide was obtained in the same manner as in the aforementioned Example 27, except that 4-tert-butylbenzyl bromide was used instead of butyl iodide.

$^1$H-NMR (DMSO-d$_6$, 300 MHz) δ 10.32 (s, 1H), 7.77 (d, 2H), 7.62 (m, 2H), 7.34 (s, 1H), 7.01 (s, 2H), 6.93 (s, 2H), 6.86 (s, 1H), 5.98 (s, 2H), 5.62 (s, 2H), 5.22 (broad t, 2H), 4.63 (s, 2H), 4.02 (s, 3H), 3.24 (t, 2H), 1.32 (s, 9H).

EXAMPLE 30

13-(3,4,5-trimethoxybenzyl)-9-O-butylberberrubine iodide (Compound No. 30)

0.2 g of 13-(3,4,5-trimethoxybenzyl)berberrubine obtained in the aforementioned Example 2 was dissolved in 50 mL of acetonitrile (CH$_3$CN). After completely the mixture dissolving by string at 120° C., a reaction was performed for 4 hours by slowly adding 0.1 mL of butyl iodide dropwise. The reaction solution was concentrated under reduced pressure. 0.08 g of 13-(3,4, 5-trimethoxybenzyl)-9-O-butylberberrubine iodide was obtained from silica gel column chromatography (1:9/ MeOH:CHCl$_3$).

¹H-NMR (DMSO-d₆, 300 MHz) δ 10.28 (s, 1H), 7.65 (s, 1H), 7.36 (s, 1H), 7.03 (s, 1H), 6.96 (s, 2H), 6.83 (s, 1H), 5.96 (s, 2H), 5.28 (broad t, 2H), 4.62 (s, 2H), 4.52 (t, 2H), 4.05(s, 6H), 4.03 (s, 3H), 3.33 (t, 2H), 2.07 (m, 2H), 1.64 (m, 2H), 1.03 (t, 3H).

EXAMPLE 31

13-(3,4,5-Trimethoxybenzyl)-9-O-hexylberberrubine iodide (Compound No. 31)

0.09 g of 13-(3,4,5-trimethoxybenzyl)-9-O-hexylberberrubine iodide was obtained in the same manner as in the aforementioned Example 30, except that hexyl iodide was used instead of butyl iodide.

¹H-NMR (DMSO-d₆, 300 MHz) δ 10.31 (s, 1H), 7.64 (s, 1H), 7.33 (s, 1H), 7.03 (s, 1H), 6.92 (s, 2H), 6.85 (s, 1H), 5.97 (s, 2H), 5.32 (broad t, 2H), 4.63 (s, 4.56 (t, 2H), 4.04(s, 6H), 4.02 (s, 3H), 3.24 (t, 2H), 2.05 (m, 2H), 1.41-1.79 (m, 6H), 1.05 (t, 3H).

EXAMPLE 32

13-(3,4,5-Trimethoxybenzyl)-9-O-(4-tert-butylbenzyl)berberrubine bromide (Compound No. 32)

0.1 g of 13-(3,4,5-trimethoxybenzyl)-9-O-(4-tert-butylbenzyl)berberrubine bromide was obtained in the same manner as in the aforementioned Example 30, except that 4-tert-butylbenzyl bromide was used instead of butyl iodide.

¹H-NMR (DMSO-d₆, 300 MHz) δ 10.31 (s, 1H), 7.76 (d, 2H), 7.63 (m, 2H), 7.34 (s, 1H), 7.01 (s, 2H), 6.93 (s, 2H), 6.86 (s, 1H), 5.98 (s, 2H), 5.61 (s, 2H), 5.22 (broad t, 2H), 4.65 (s, 2H), 4.04(s, 6H), 4.02 (s, 3H), 3.24 (t, 2H), 1.33 (s, 9H).

EXAMPLE 33

13-(4-Trifluoromethoxybenzyl)-9-O-butylberberrubine iodide (Compound No. 33)

0.2 g of 13-(4-trifluoromethoxybenzyl)berberrubine obtained in the aforementioned Example 3 was dissolved in 50 mL of acetonitrile (CH₃CN). After completely dissolving the mixture by string at 120° C., a reaction was performed for 4 hours by slowly adding 0.1 mL of butyl iodide dropwise. The reaction solution was concentrated under reduced pressure. 0.08 g of 13-(4-trifluoromethoxybenzyl)-9-O-butylberberrubine iodide was obtained from silica gel column chromatography (1:9/MeOH:CHCl₃).

¹H-NMR (DMSO-d₆, 300 MHz) δ 10.27 (s, 1H), 7.64 (m, 2H), 7.36 (d, 2H), 7.02 (s, 1H), 6.98 (s, 2H), 6.87 (s, 1H), 5.99 (s, 2H), 5.38 (broad t, 2H), 4.62 (s, 2H), 4.57 (t, 2H), 4.00 (s, 3H), 3.27 (t, 2H), 2.07 (m, 2H), 1.63 (m, 2H), 1.03 (t, 3H).

EXAMPLE 34

13-(4-Trifluoromethoxybenzyl)-9-O-hexylberberrubine iodide (Compound No. 34)

0.09 g of 13-(4-trifluoromethoxybenzyl)-9-O-hexylberberrubine iodide was obtained in the same manner as in the aforementioned Example 33, except that hexyl iodide was used instead of butyl iodide.

¹H-NMR (DMSO-d₆, 300 MHz) δ 10.31 (s, 1H), 7.67 (m, 2H), 7.38 (d, 2H), 7.04 (s, 1H), 6.93 (s, 2H), 6.86 (s, 1H), 5.97 (s, 2H), 5.34 (broad t, 2H), 4.65 (s, 2H), 4.56 (t, 2H), 4.02 (s, 3H), 3.24 (t, 2H), 2.04 (m, 2H), 1.43-1.79 (m, 6H), 1.05 (t, 3H).

EXAMPLE 35

13-(4-Trifluoromethoxybenzyl)-9-O-(4-tert-butylbenzyl)berberrubine bromide (Compound No. 35)

0.1 g of 13-(4-trifluoromethoxybenzyl)-9-O-(4-tert-butylbenzyl)berberrubine bromide was obtained in the same manner as in the aforementioned Example 33, except that 4-tert-butylbenzyl bromide was used instead of butyl iodide.

¹H-NMR (DMSO-d₆, 300 MHz) δ 10.34 (s, 1H), 7.77 (d, 2H), 7.66 (m, 2H), 7.36 (d, 2H), 7.27(s, 2H), 7.02 (d, 2H), 6.98 (s, 1H), 6.86 (s, 1H), 5.97 (s, 2H), 5.62 (s, 2H), 5.22 (broad t, 2H), 4.62 (s, 2H), 4.03 (s, 3H), 3.31 (t, 2H), 1.32 (s, 9H).

EXAMPLE 36

13-(4-Trifluoromethylbenzyl)-9-O-butylberberrubine iodide (Compound No. 36)

0.2 g of 13-(4-trifluoromethylbenzyl)berberrubine obtained in the aforementioned Example 4 was dissolved in 50 mL of acetonitrile (CH₃CN). After completely dissolving the mixture by string at 120° C., a reaction was performed for 4 hours by slowly adding 0.1 mL of butyl iodide dropwise. The reaction solution was concentrated under reduced pressure. 0.08 g of 13-(4-trifluoromethylbenzyl)-9-O-butylberberrubine iodide was obtained from silica gel column chromatography (1:9/MeOH:CHCl₃).

¹H-NMR (DMSO-d₆, 300 MHz) δ 10.25 (s, 1H), 7.64 (m, 2H), 7.35 (d, 2H), 7.02 (s, 1H), 6.98 (s, 2H), 6.85 (s, 1H), 5.99 (s, 2H), 5.35 (broad t, 2H), 4.62 (s, 2H), 4.57 (t, 2H), 4.00 (s, 3H), 3.27 (t, 2H), 2.07 (m, 2H), 1.63 (m, 2H), 1.03 (t, 3H).

EXAMPLE 37

13-(4-Trifluoromethylbenzyl)-9-O-hexylberberrubine iodide (Compound No. 37)

0.09 g of 13-(4-trifluoromethylbenzyl)-9-O-hexylberberrubine iodide was obtained in the same manner as in the aforementioned Example 36, except that hexyl iodide was used instead of butyl iodide.

¹H-NMR (DMSO-d₆, 300 MHz) δ 10.33 (s, 1H), 7.65 (m, 2H), 7.38 (d, 2H), 7.03 (s, 1H), 6.93 (s, 2H), 6.86 (s, 1H), 5.97 (s, 2H), 5.35 (broad t, 2H), 4.63 (s, 2H), 4.56 (t, 2H), 4.02 (s, 3H), 3.24 (t, 2H), 2.04 (m, 2H), 1.44-1.79 (m, 6H), 1.03 (t, 3H).

EXAMPLE 38

13-(4-Trifluoromethylbenzyl)-9-O-(4-tert-butylbenzyl)berberrubine bromide (Compound No. 38)

0.09 g of 13-(4-trifluoromethylbenzyl)-9-O-(4-tert-butylbenzyl)berberrubine bromide was obtained in the same manner as in the aforementioned Example 36, except that 4-tert-butylbenzyl bromide was used instead of butyl iodide.

¹H-NMR (DMSO-d₆, 300 MHz) δ 10.33 (s, 1H), 7.76 (d, 2H), 7.64 (m, 2H), 7.36 (d, 2H), 7.27(s, 2H), 7.02 (d, 2H), 6.98 (s, 1H), 6.86 (s, 1H), 5.97 (s, 2H), 5.64 (s, 2H), 5.22 (broad t, 2H), 4.62 (s, 2H), 4.03 (s, 3H), 3.31 (t, 2H), 1.34 (s, 9H).

EXAMPLE 39

13-(4-tert-Butylbenzyl)-9-O-propylberberrubine chloride (Compound No. 39)

0.2 g of 13-(4-tert-butylbenzyl)-9-O-propylberberrubine iodide obtained in the aforementioned Example 7 was dissolved in methanol (MeOH) and 0.1 g of silver chloride (AgCl) was added. After stirring the mixture at 60° C. for 1 hour, the reaction solution was filtered and concentrated under reduced pressure to obtain 0.18 g of 13-(4-tert-butylbenzyl)-9-O-propylberberrubine chloride.

$^1$H-NMR (DMSO-$d_6$, 300 MHz) δ 10.27 (s, 1H), 7.63 (m, 2H), 7.32 (d, 2H), 7.02 (s, 1H), 6.96 (s, 2H), 6.84 (s, 1H), 5.96 (s, 2H), 5.36 (broad t, 2H), 4.63 (s, 2H), 4.54 (t, 2H) 4.02 (s, 3H) 3.31 (t, 2H) 2.04 (m, 2H), 1.35 (s, 9H), 1.04 (t, 3H).

EXAMPLE 40

13-(4-tert-Butylbenzyl)-9-O-butylberberrubine chloride (Compound No. 40)

0.2 g of 13-(4-tert-butylbenzyl)-9-O-butylberberrubine iodide obtained in the aforementioned Example 8 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-tert-butylbenzyl)-9-O-butylberberrubine chloride.

$^1$H-NMR (DMSO-$d_6$, 300 MHz) δ 10.27 (s, 1H), 7.64 (m, 2H), 7.36 (d, 2H), 7.02 (s, 1H), 6.98 (s, 214), 6.87 (s, 1H), 5.99 (s, 2H), 5.38 (broad t, 2H), 4.62 (s, 2H), 4.57 (t, 2H), 4.00 (s, 3H), 3.27 (t, 2H), 2.07 (m, 2H), 1.63 (m, 2H), 1.32 (s, 9H), 1.03 (t, 3H).

EXAMPLE 41

13-(4-tert-Butylbenzyl)-9-O-hexylberberrubine chloride (Compound No. 41)

0.2 g of 13-(4-tert-butylbenzyl)-9-O-hexylberberrubine iodide obtained in the aforementioned Example 9 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-tert-butylbenzyl)-9-O-hexylberberrubine chloride.

$^1$H-NMR (DMSO-$d_6$, 300 MHz) δ 10.31 (s, 1H), 7.67 (m, 2H), 7.38 (d, 2H), 7.04 (s, 1H), 6.93 (s, 214), 6.86 (s, 1H), 5.97 (s, 2H), 5.34 (broad t, 2H), 4.65 (s, 2H), 4.56 (t, 2H), 4.02 (s, 3H), 3.24 (t, 2H), 2.04 (m, 2H), 1.43-1.79 (m, 6H), 1.31 (s, 9H), 1.05 (t, 3H).

EXAMPLE 42

13-(4-tert-Butylbenzyl)-9-O-octylberberrubine chloride (Compound No. 42)

0.2 g of 13-(4-tert-butylbenzyl)-9-O-octylberberrubine iodide obtained in the aforementioned Example 10 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-tert-butylbenzyl)-9-O-octylberberrubine chloride.

$^1$H-NMR (DMSO-$d_6$, 300 MHz) δ 10.28 (s, 1H), 7.69 (m, 2H), 7.40 (d, 2H), 7.07 (s, 1H), 6.95 (s, 2H), 6.88 (s, 1H), 5.98 (s, 2H), 5.35 (broad t, 2H), 4.64 (s, 2H), 4.54 (t, 2H) 4.04 (s, 3H) 3.25 (t, 2H) 2.06 (m, 2H), 1.44-1.80 (m, 1011), 1.33 (s, 9H), 1.03 (t, 3H).

EXAMPLE 43

13-(4-tert-Butylbenzyl)-9-O-(3-hydroxypropyl)berberrubine chloride (Compound No. 43)

0.2 g of 13-(4-tert-butylbenzyl)-9-O-(3-hydroxypropyl)berberrubine iodide obtained in the aforementioned Example 11 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-tert-butylbenzyl)-9-O-(3-hydroxypropyl)berberrubine chloride.

$^1$H-NMR (DMSO-$d_6$, 300 MHz) δ 10.56 (s, 1H), 7.65 (m, 2H), 7.37 (d, 2H), 7.03 (s, 1H), 7.00 (s, 2H), 6.87 (s, 1H), 6.00 (s, 2H), 5.20 (broad t, 2H), 4.69 (t, 2H), 4.63 (s, 2H), 4.05(t, 2H), 4.02 (s, 3H) 3.28 (t, 2H) 2.25 (m, 2H), 1.32 (s, 9H).

EXAMPLE 44

13-(4-tert-Butylbenzyl)-9-O-(6-chlorohexyl)berberrubine chloride (Compound No. 44)

0.2 g of 13-(4-tert-butylbenzyl)-9-O-(6-chlorohexyl)berberrubine iodide obtained in the aforementioned Example 12 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-tert-butylbenzyl)-9-O-(6-chlorohexyl)berberrubine chloride.

$^1$H-NMR (DMSO-$d_6$, 300 MHz) δ 10.30 (s, 1H), 7.66 (m, 2H), 7.35 (d, 2H), 7.02 (d, 2H), 7.00 (s, 1H), 6.87 (s, 1H), 6.00 (s, 2H), 5.21 (broad t, 2H), 4.63 (s, 2H), 4.61 (t, 2H), 4.01 (s, 3H), 3.60 (t 2H), 3.30 (t, 2H) 2.10 (m, 2H), 1.89 (m, 2H), 1.58-1.64 (m, 4H), 1.32 (s, 9H).

EXAMPLE 45

13-(4-tert-Butylbenzyl)-9-O-allylberberrubine chloride (Compound No. 45)

0.2 g of 13-(4-tert-butylbenzyl)-9-O-allylberberrubine iodide obtained in the aforementioned Example 13 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-tert-butylbenzyl)-9-O-allylberberrubine $^1$H-NMR (DMSO-$d_6$, 300 MHz) δ 10.55 (s, 1H), 7.65 (m, 2H), 7.36 (d, 2H), 7.03 (d, 2H), 6.99 (s, 1H), 6.87 (s, 1H), 6.49(m, 1H), 6.00 (s, 2H), 5.5 (dd, 1H), 5.33 (dd, 1H), 5.13 (d, 2H), 4.62 (s, 2H), 4.01 (s, 3H) 3.29 (t, 2H), 1.32 (s, 9H).

EXAMPLE 46

13-(4-tert-Butylbenzyl)-9-O-crotylberberrubine chloride (Compound No. 46)

0.2 g of 13-(4-tert-butylbenzyl)-9-O-crotylberberrubine iodide obtained in the aforementioned Example 14 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-tert-butylbenzyl)-9-O-crotylberberrubine chloride.

$^1$H-NMR (DMSO-d$_6$, 300 MHz) δ 10.52 (s, 1H), 7.64 (m, 2H), 7.36 (d, 2H), 7.02 (d, 2H), 6.99 (s, 1H), 6.87 (s, 1H), 6.12(m, 2H), 6.00 (s, 2H), 5.31 (broad, 2H), 5.06 (d, 2H), 4.62 (s, 2H), 4.01 (s, 3H) 3.30 (t, 2H), 1.77 (d, 3H), 1.32 (s, 9H).

EXAMPLE 47

13-(4-tert-Butylbenzyl)-9-O-(4-tert-butylbenzyl) berberrubine chloride (Compound No. 47)

0.2 g of 13-(4-tert-butylbenzyl)-9-O-(4-tert-butylbenzyl) berberrubine iodide obtained in the aforementioned Example 15 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-tert-butylbenzyl)-9-O-(4-tert-butylbenzyl)berberrubine chloride.

$^1$H-NMR (DMSO-d$_6$, 300 MHz) δ 10.34 (s, 1H), 7.77 (d, 2H), 7.66 (m, 2H), 7.36 (d, 2H), 7.27(s, 2H), 7.02 (d, 2H), 6.98 (s, 1H), 6.86 (s, 1H), 5.97 (s, 2H), 5.62 (s, 2H), 5.22 (broad t, 2H), 4.62 (s, 2H), 4.03 (s, 3H), 3.31 (t, 2H), 1.34 (s, 9H), 1.32 (s, 9H).

EXAMPLE 48

13-(4-tert-Butylbenzyl)-9-O-(4-isopropylbenzyl) berberrubine chloride (Compound No. 48)

0.2 g of 13-(4-tert-butylbenzyl)-9-O-(4-isopropylbenzyl) berberrubine iodide obtained in the aforementioned Example 16 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-tert-butylbenzyl)-9-O-(4-isopropylbenzyl)berberrubine chloride.

$^1$H-NMR (DMSO-d$_6$, 300 MHz) δ 10.38 (s, 1H), 7.77 (d, 2H), 7.67 (m, 2H), 7.36 (d, 2H), 7.28(s, 2H), 7.02 (d, 2H), 6.98 (s, 1H), 6.86 (s, 1H), 5.99 (s, 2H), 5.63 (s, 2H), 5.20 (broad t, 2H), 4.62 (s, 2H), 4.04 (s, 3H), 3.30 (t, 2H), 2.91 (m, 1H), 1.32 (s, 9H), 1.24 (d, 6H).

EXAMPLE 49

13-(4-Isopropylbenzyl)-9-O-propylberberrubine chloride (Compound No. 49)

0.2 g of 13-(4-isopropylbenzyl)-9-O-propylberberrubine iodide obtained in the aforementioned Example 17 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-isopropylbenzyl)-9-O-propylberberrubine chloride.

$^1$H-NMR (DMSO-d$_6$, 300 MHz) δ 10.26 (s, 1H), 7.64 (m, 2H), 7.36 (d, 2H), 7.01 (s, 1H), 6.96 (s, 2H), 6.83 (s, 1H), 5.96 (s, 2H), 5.32 (broad t, 2H), 4.64 (s, 2H), 4.53 (t, 2H), 4.02 (s, 3H), 3.32 (t, 2H), 2.91 (m, 1H), 2.04 (m, 2H), 1.25 (d, 6H), 1.04 (t, 3H).

EXAMPLE 50

13-(4-Isopropylbenzyl)-9-O-butylberberrubine chloride (Compound No. 50)

0.2 g of 13-(4-isopropylbenzyl)-9-O-butylberberrubine iodide obtained in the aforementioned Example 18 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-isopropylbenzyl)-9-O-butylberberrubine chloride.

$^1$H-NMR (DMSO-d$_6$, 300 MHz) δ 10.31 (s, 1H), 7.63 (m, 2H), 7.36 (d, 2H), 7.02 (s, 1H), 6.98 (s, 2H), 6.87 (s, 1H), 5.99 (s, 2H), 5.38 (broad t, 2H), 4.64 (s, 2H), 4.52 (t, 2H), 4.00 (s, 3H), 3.27 (t, 2H), 2.91 (m, 1H), 2.07 (m, 2H), 1.63 (m, 2H), 1.26 (d, 6H), 1.04 (t, 3H).

EXAMPLE 51

13-(4-Isopropylbenzyl)-9-O-hexylberberrubine chloride (Compound No. 51)

0.2 g of 13-(4-isopropylbenzyl)-9-O-hexylberberrubine iodide obtained in the aforementioned Example 19 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-isopropylbenzyl)-9-O-hexylberberrubine chloride.

$^1$H-NMR (DMSO-d$_6$, 300 MHz) δ 10.32 (s, 1H), 7.67 (m, 2H), 7.36 (d, 2H), 7.04 (s, 1H), 6.93 (s, 2H), 6.86 (s, 1H), 5.97 (s, 2H), 5.34 (broad t, 2H), 4.65 (s, 2H), 4.56 (t, 2H), 4.02 (s, 3H), 3.24 (t, 2H), 2.91 (m, 1H), 2.04 (m, 2H), 1.43-1.78 (m, 6H), 1.25 (d, 6H), 1.05 (t, 3H).

EXAMPLE 52

13-(4-Isopropylbenzyl)-9-O-octylberberrubine chloride (Compound No. 52)

0.2 g of 13-(4-isopropylbenzyl)-9-O-octylberberrubine iodide obtained in the aforementioned Example 20 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-isopropylbenzyl)-9-O-octylberberrubine chloride.

$^1$H-NMR (DMSO-d$_6$, 300 MHz) δ 10.28 (s, 1H), 7.69 (m, 2H), 7.40 (d, 2H), 7.07 (s, 1H), 6.95 (s, 2H), 6.88 (s, 1H), 5.98 (s, 2H), 5.35 (broad t, 2H), 4.64 (s, 2H), 4.54 (t, 2H) 4.04 (s, 3H) 3.25 (t, 2H) 2.92 (m, 1H), 2.06 (m, 2H), 1.44-1.81 (m, 10H), 1.27 (d, 6H), 1.03 (t, 3H).

EXAMPLE 53

13-(4-Isopropylbenzyl)-9-O-(3-hydroxypropyl)berberrubine chloride (Compound No. 53)

0.2 g of 13-(4-isopropylbenzyl)-9-O-(3-hydroxypropyl) berberrubine iodide obtained in the aforementioned Example 21 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-isopropylbenzyl)-9-O-(3-hydroxypropyl)berberrubine chloride.

$^1$H-NMR (DMSO-d$_6$, 300 MHz) δ 10.26 (s, 1H), 7.65 (m, 2H), 7.37 (d, 2H), 7.03 (s, 1H), 7.00 (s, 2H), 6.87 (s, 1H), 6.00 (s, 2H), 5.20 (broad t, 2H), 4.69 (t, 2H), 4.63 (s, 2H), 4.05(t, 2H), 4.02 (s, 3H), 3.28 (t, 2H), 2.90 (m, 1H), 2.25 (m, 2H), 1.27 (d, 6H).

EXAMPLE 54

13-(4-Isopropylbenzyl)-9-O-(6-chlorohexyl)berberrubine chloride (Compound No. 54)

0.2 g of 13-(4-isopropylbenzyl)-9-O-(6-chlorohexyl)berberrubine iodide obtained in the aforementioned Example 22 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-isopropylbenzyl)-9-O-(6-chlorohexyl)berberrubine chloride.

$^1$H-NMR (DMSO-$d_6$, 300 MHz) δ 10.30 (s, 1H), 7.66 (m, 2H), 7.35 (d, 2H), 7.02 (d, 2H), 7.00 (s, 1H), 6.87 (s, 1H), 6.00 (s, 2H), 5.21 (broad t, 2H), 4.63 (s, 2H), 4.61 (t, 2H), 4.01 (s, 3H), 3.60 (t 2H), 3.30 (t, 2H), 2.91 (m, 1H), 2.10 (m, 2H), 1.89 (m, 2H), 1.58-1.64 (m, 4H), 1.28 (d, 6H).

EXAMPLE 55

13-(4-Isopropylbenzyl)-9-O-allylberberrubine chloride (Compound No. 55)

0.2 g of 13-(4-isopropylbenzyl)-9-O-allylberberrubine iodide obtained in the aforementioned Example 23 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-isopropylbenzyl)-9-O-allylberberrubine chloride.

$^1$H-NMR (DMSO-$d_6$, 300 MHz) δ 10.25 (s, 1H), 7.65 (m, 2H), 7.36 (d, 2H), 7.03 (d, 2H), 6.99 (s, 1H), 6.87 (s, 1H), 6.49(m, 1H), 6.00 (s, 2H), 5.5 (dd, 1H), 5.33 (dd, 1H), 5.13 (d, 2H), 4.62 (s, 2H), 4.01 (s, 3H) 3.29 (t, 2H), 2.92 (m, 1H), 1.26 (d, 6H).

EXAMPLE 56

13-(4-isopropylbenzyl)-9-O-crotylberberrubine chloride (Compound No. 56)

0.2 g of 13-(4-isopropylbenzyl)-9-O-crotylberberrubine iodide obtained in the aforementioned Example 24 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-isopropylbenzyl)-9-O-crotylberberrubine chloride.

$^1$H-NMR (DMSO-$d_6$, 300 MHz) δ 10.30 (s, 1H), 7.64 (m, 2H), 7.36 (d, 2H), 7.02 (d, 2H), 6.99 (s, 1H), 6.87 (s, 1H), 6.12(m, 2H), 6.00 (s, 2H), 5.31 (broad, 2H), 5.06 (d, 2H), 4.62 (s, 2H), 4.01 (s, 3H) 3.30 (t, 2H), 2.91 (m, 1H), 1.77 (d, 3H), 1.26 (d, 6H).

EXAMPLE 57

13-(4-Isopropylbenzyl)-9-O-(4-tert-butylbenzyl) berberrubine chloride (Compound No. 57)

0.2 g of 13-(4-isopropylbenzyl)-9-O-(4-tert-butylbenzyl) berberrubine iodide obtained in the aforementioned Example 25 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-isopropylbenzyl)-9-O-(4-tert-butylbenzyl)berberrubine chloride.

$^1$H-NMR (DMSO-$d_6$, 300 MHz) δ 10.34 (s, 1H), 7.77 (d, 2H), 7.66 (m, 2H), 7.36 (d, 2H), 7.27(s, 2H), 7.02 (d, 2H), 6.98 (s, 1H), 6.86 (s, 1H), 5.97 (s, 2H), 5.62 (s, 2H), 5.22 (broad t, 2H), 4.62 (s, 2H), 4.03 (s, 3H), 3.31 (t, 2H), 2.91 (m, 1H), 1.32 (s, 9H), 1.26 (d, 6H).

EXAMPLE 58

13-(4-Isopropylbenzyl)-9-O-(4-isopropylbenzyl) berberrubine chloride (Compound No. 58)

0.2 g of 13-(4-isopropylbenzyl)-9-O-(4-isopropylbenzyl) berberrubine iodide obtained in the aforementioned Example 26 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-isopropylbenzyl)-9-O-(4-isopropylbenzyl)berberrubine chloride.

$^1$H-NMR (DMSO-$d_6$, 300 MHz) δ 10.31 (s, 1H), 7.78 (d, 2H), 7.67 (m, 2H), 7.36 (d, 2H), 7.28(s, 2H), 7.02 (d, 2H), 6.98 (s, 1H), 6.85 (s, 1H), 5.99 (s, 2H), 5.63 (s, 2H), 5.20 (broad t, 2H), 4.62 (s, 2H), 4.04 (s, 3H), 3.30 (t, 2H) 2.91 (m, 2H), 1.27 (d, 6H), 1.24 (d, 6H).

EXAMPLE 59

13-(3,4,5-trifluorobenzyl)-9-O-butylberberrubine chloride (Compound No. 59)

0.2 g of 13-(3,4,5-trifluorobenzyl)-9-O-butylberberrubine iodide obtained in the aforementioned Example 27 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(3,4,5-trifluorobenzyl)-9-O-butylberberrubine chloride.

$^1$H-NMR (DMSO-$d_6$, 300 MHz) δ 10.26 (s, 1H), 7.64 (s, 1H), 7.36 (s, 1H), 7.01 (s, 1H), 6.96 (s, 2H), 6.83 (s, 1H), 5.96 (s, 2H), 5.34 (broad t, 2H), 4.63 (s, 2H), 4.52 (t, 2H), 4.01 (s, 3H), 3.33 (t, 2H), 2.07 (m, 2H), 1.63 (m, 2H), 1.04 (t, 3H).

EXAMPLE 60

13-(3,4,5-Trifluorobenzyl)-9-O-hexylberberrubine chloride (Compound No. 60)

0.2 g of 13-(3,4,5-trifluorobenzyl)-9-O-hexylberberrubine iodide obtained in the aforementioned Example 28 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(3,4,5-trifluorobenzyl)-9-O-hexylberberrubine chloride.

$^1$H-NMR (DMSO-$d_6$, 300 MHz) δ 10.32 (s, 1H), 7.62 (s, 1H), 7.34 (s, 1H), 7.01 (s, 1H), 6.93 (s, 2H), 6.86 (s, 1H), 5.97 (s, 2H), 5.34 (broad t, 2H), 4.65 (s, 2H), 4.56 (t, 2H), 4.02 (s, 3H), 3.24 (t, 2H), 2.04 (m, 2H), 1.43-1.78 (m, 6H), 1.05 (t, 3H).

EXAMPLE 61

13-(3,4,5-Trifluorobenzyl)-9-O-(4-tert-butylbenzyl) berberrubine chloride (Compound No. 61)

0.2 g of 13-(3,4,5-trifluorobenzyl)-9-O-(4-tert-butylbenzyl)berberrubine iodide obtained in the aforementioned Example 29 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(3,4,5-trifluorobenzyl)-9-O-(4-tert-butylbenzyl)berberrubine chloride.

$^1$H-NMR (DMSO-$d_6$, 300 MHz) δ 10.32 (s, 1H), 7.77 (d, 2H), 7.62 (m, 2H), 7.34 (s, 1H), 7.01 (s, 2H), 6.93 (s, 2H), 6.86 (s, 1H), 5.98 (s, 2H), 5.62 (s, 2H), 5.22 (broad t, 2H), 4.63 (s, 2H), 4.02 (s, 3H), 3.24 (t, 2H), 1.32 (s, 9H).

EXAMPLE 62

13-(3,4,5-Trimethoxybenzyl)-9-O-butylberberrubine chloride (Compound No. 62)

0.2 g of 13-(3,4,5-trimethoxybenzyl)-9-O-butylberberrubine iodide obtained in the aforementioned Example 30 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(3,4,5-trimethoxybenzyl)-9-O-butylberberrubine chloride.

$^1$H-NMR (DMSO-$d_6$, 300 MHz) δ 10.28 (s, 1H), 7.65 (s, 1H), 7.36 (s, 1H), 7.03 (s, 1H), 6.96 (s, 2H), 6.83 (s, 1H), 5.96 (s, 2H), 5.28 (broad t, 2H), 4.62 (s, 2H), 4.52 (t, 2H), 4.05 (s, 6H), 4.03 (s, 3H), 3.33 (t, 2H), 2.07 (m, 2H), 1.64 (m, 2H), 1.03 (t, 3H).

EXAMPLE 63

13-(3,4,5-Trimethoxybenzyl)-9-O-hexylberberrubine chloride (Compound No. 63)

0.2 g of 13-(3,4,5-trimethoxybenzyl)-9-O-hexylberberrubine iodide obtained in the aforementioned Example 31 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(3,4,5-trimethoxybenzyl)-9-O-hexylberberrubine chloride.

$^1$H-NMR (DMSO-$d_6$, 300 MHz) δ 10.31 (s, 1H), 7.64 (s, 1H), 7.33 (s, 1H), 7.03 (s, 1H), 6.92 (s, 2H), 6.85 (s, 1H), 5.97 (s, 2H), 5.32 (broad t, 2H), 4.63 (s, 2H), 4.56 (t, 2H), 4.04 (s, 6H), 4.02 (s, 3H), 3.24 (t, 2H), 2.05 (m, 2H), 1.41-1.79 (m, 6H), 1.05 (t, 3H).

EXAMPLE 64

13-(3,4,5-Trimethoxybenzyl)-9-O-(4-tert-butylbenzyl)berberrubine chloride (Compound No. 64)

0.2 g of 13-(3,4,5-trimethoxybenzyl)-9-O-(4-tert-butylbenzyl)berberrubine iodide obtained in the aforementioned Example 32 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(3,4,5-trimethoxybenzyl)-9-O-(4-tert-butylbenzyl)berberrubine chloride.

$^1$H-NMR (DMSO-$d_6$, 300 MHz) δ 10.31 (s, 1H), 7.76 (d, 2H), 7.63 (m, 2H), 7.34 (s, 1H), 7.01 (s, 2H), 6.93 (s, 2H), 6.86 (s, 1H), 5.98 (s, 2H), 5.61 (s, 2H), 5.22 (broad t, 2H), 4.65 (s, 2H), 4.04(s, 6H), 4.02 (s, 3H), 3.24 (t, 2H), 1.33 (s, 9H).

EXAMPLE 65

13-(4-Trifluoromethoxybenzyl)-9-O-butylberberrubine chloride (Compound No. 65)

0.2 g of 13-(4-trifluoromethoxybenzyl)-9-O-butylberberrubine iodide obtained in the aforementioned Example 33 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-trifluoromethoxybenzyl)-9-O-butylberberrubine chloride.

$^1$H-NMR (DMSO-$d_6$, 300 MHz) δ : 10.27 (s, 1H), 7.64 (m, 2H), 7.36 (d, 2H), 7.02 (s, 1H), 6.98 (s, 2H), 6.87 (s, 1H), 5.99 (s, 2H), 5.38 (broad t, 2H), 4.62 (s, 2H), 4.57 (t, 2H), 4.00 (s, 3H), 3.27 (t, 2H), 2.07 (m, 2H), 1.63 (m, 2H), 1.03 (t, 3H).

EXAMPLE 66

13-(4-Trifluoromethoxybenzyl)-9-O-hexylberberrubine chloride (Compound No. 66)

0.2 g of 13-(4-trifluoromethoxybenzyl)-9-O-hexylberberrubine iodide obtained in the aforementioned Example 34 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-trifluoromethoxybenzyl)-9-O-hexylberberrubine chloride.

$^1$H-NMR (DMSO-$d_6$, 300 MHz) δ 10.31 (s, 1H), 7.67 (m, 2H), 7.38 (d, 2H), 7.04 (s, 1H), 6.93 (s, 2H), 6.86 (s, 1H), 5.97 (s, 2H), 5.34 (broad t, 2H), 4.65 (s, 2H), 4.56 (t, 2H), 4.02 (s, 3H), 3.24 (t, 2H), 2.04 (m, 2H), 1.43-1.79 (m, 6H), 1.05 (t, 3H).

EXAMPLE 67

13-(4-Trifluoromethoxybenzyl)-9-O-(4-tert-butylbenzyl)berberrubine chloride (Compound No. 67)

0.2 g of 13-(4-trifluoromethoxybenzyl)-9-O-(4-tert-butylbenzyl)berberrubine iodide obtained in the aforementioned Example 35 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-trifluoromethoxybenzyl)-9-O-(4-tert-butylbenzyl)berberrubine chloride.

$^1$H-NMR (DMSO-$d_6$, 300 MHz) δ 10.34 (s, 1H), 7.77 (d, 2H), 7.66 (m, 2H), 7.36 (d, 2H), 7.27(s, 2H), 7.02 (d, 2H), 6.98 (s, 1H), 6.86 (s, 1H), 5.97 (s, 2H), 5.62 (s, 2H), 5.22 (broad t, 2H), 4.62 (s, 2H), 4.03 (s, 3H), 3.31 (t, 2H), 1.32 (s, 9H).

EXAMPLE 68

13-(4-Trifluoromethylbenzyl)-9-O-butylberberrubine chloride (Compound No. 68)

0.2 g of 13-(4-trifluoromethylbenzyl)-9-O-butylberberrubine iodide obtained in the aforementioned Example 36 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-trifluoromethylbenzyl)-9-O-butylberberrubine chloride.

$^1$H-NMR (DMSO-$d_6$, 300 MHz) δ 10.25 (s, 1H), 7.64 (m, 2H), 7.35 (d, 2H), 7.02 (s, 1H), 6.98 (s, 2H), 6.85 (s, 1H), 5.99 (s, 2H), 5.35 (broad t, 2H), 4.62 (s, 2H), 4.57 (t, 2H), 4.00 (s, 3H), 3.27 (t, 2H), 2.07 (m, 2H), 1.63 (m, 2H), 1.03 (t, 3H).

EXAMPLE 69

13-(4-Trifluoromethylbenzyl)-9-O-hexylberberrubine chloride (Compound No. 69)

0.2 g of 13-(4-trifluoromethylbenzyl)-9-O-hexylberberrubine iodide obtained in the aforementioned Example 37 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-trifluoromethylbenzyl)-9-O-hexylberberrubine chloride.

$^1$H-NMR (DMSO-$d_6$, 300 MHz) δ 10.33 (s, 1H), 7.65 (m, 2H), 7.38 (d, 2H), 7.03 (s, 1H), 6.93 (s, 2H), 6.86 (s, 1H), 5.97 (s, 2H), 5.35 (broad t, 2H), 4.63 (s, 2H), 4.56 (t, 2H), 4.02 (s, 3H), 3.24 (t, 2H), 2.04 (m, 2H), 1.44-1.79 (m, 6H), 1.03 (t, 3H).

EXAMPLE 70

13-(4-Trifluoromethylbenzyl)-9-O-(4-tert-butylbenzyl)berberrubine chloride (Compound No. 70)

0.2 g of 13-(4-trifluoromethylbenzyl)-9-O-(4-tert-butylbenzyl)berberrubine iodide obtained in the aforementioned Example 38 was dissolved in methanol (MeOH) and 0.1 g of silver chloride (AgCl) was added. After stirring at 60° C. for 1 hour, the reaction solution was filtered and concentrated under reduced pressure to obtain 0.18 g of 13-(4-trifluoromethylbenzyl)-9-O-(4-tert-butylbenzyl)berberrubine chloride.

$^1$H-NMR (DMSO-$d_6$, 300 MHz) δ 10.33 (s, 1H), 7.76 (d, 2H), 7.64 (m, 2H), 7.36 (d, 2H), 7.27(s, 2H), 7.02 (d, 2H), 6.98 (s, 1H), 6.86 (s, 1H), 5.97 (s, 2H), 5.64 (s, 2H), 5.22 (broad t, 2H), 4.62 (s, 2H), 4.03 (s, 3H), 3.31 (t, 2H), 1.34 (s, 9H).

The novel compound of the present invention represented by the formula (1) can be prepared into various preparation forms depending on the purposes specified. Some non-restrictive preparation examples of the compound of the present invention represented by the aforementioned formula (1) are given below.

Preparation Examples

Preparation Example 1

Tablets (Direct Pressing)

5.0 mg of the active ingredient was sieved and mixed with 14.1 mg of lactose, 0.8 mg of Crospovidone USNF and 0.1 mg of magnesium stearate. The mixture was pressed to form a tablet.

Preparation Example 2

Tablets (Wet Granulation)

5.0 mg of the active ingredient was sieved and mixed with 16.0 mg of lactose and 4.0 mg of starch. A solution obtained by dissolving 80 0.3 mg of polysorbate in pure water was added and the resultant mixture was granulated. After drying, the resultant granule was sieved and mixed with 2.7 mg of colloidal silicon dioxide and 2.0 mg of magnesium stearate. The granule was pressed to form a tablet.

Preparation Example 3

Powder and Capsule 5.0 mg of the active ingredient was sieved and mixed with 14.8 mg of lactose, 10.0 mg of polyvinylpyrrolidone and 0.2 mg of magnesium stearate. The mixture was filled into a No. 5 gelatin capsule using a suitable apparatus.

Preparation Example 4

Injection Form

An injection form was prepared by mixing 100 mg of the active ingredient, 180 mg of mannitol, 26 mg of $Na_2HPO_4.12H_2O$ and 2974 mg of distilled water.

The inhibitory activity against chitin synthase and antifungal activity against human pathogenic fungi of the novel compound in accordance with the present invention were tested as follows.

TEST EXAMPLES

Test Example 1

Preparation of Chitin Synthase 1 Crude Enzyme of *Candida albicans*

Crude enzyme was prepared using the *Candida albicans* chs2 Δ chs 3 Δ mutant (chs2 Δ::hisG/chs2 Δ::hisG chs3 Δ::hisG/chs3 Δ::hisG) strain, which can only produce the chitin synthase 1. The strain was inoculated with the SDA (Sabouraud dextrose agar) culture medium (4% dextrose, 1% peptone, pH 5.6) and cultured at 30° C. for 15-17 hours until the absorbance at 550nm reaches 0.7. The cells were collected and suspended in a 50 mM Tris-HCl (pH 7.5) buffer solution containing 5 mM magnesium acetate. After centrifugation at 8,000×g for 10 minutes, the pellets were suspended in the same Tris-HCl buffer solution. The suspension was divided into aliquots in 50 mL conical test tubes. After adding glass beads, the cells were disrupted by vigorously vortexing with an interval of 30 seconds. The cell residues were removed by centrifuging at 3,000×g for 5 minutes. The supernatant was ultra-centrifuged at 130,000×g for 1 hour. The resultant pellets were collected and suspended in 50 mM Tris-HCl (pH 7.5) containing 33% glycerol, to a final volume of 1.6 mg/g (wet weight) of yeast used. The suspension was divided into aliquots and kept at −70° C. until it is used.

Test Example 2

Preparation of Chitin Synthase 2 Crude Enzyme of *Saccharomyces cerevisiae*

Crude enzyme was prepared using the recombinant *Saccharomyces cerevisiae* ECY38-38A(pAS6) (MATa chs1-23 chs2::LEU2 cal 1/csd 2 ura 3-52 trp 1-1 leu 2-2 pAS6) strain, which can produce the chitin synthase 2 only. The strain was inoculated with the YPG culture medium (1% yeast extract, 2% peptone, 2% galactose) and cultured at 30° C. overnight.

Then, it was inoculated with a fresh YPG culture medium and cultured for 15-17 hours until the Absorbance at 550 nm reaches 1.0. The cells were collected and suspended in 50 mM Tris-HCl (pH 7.5) buffer containing 5 mM magnesium acetate. After centrifugation at 8,000×g for 10 minutes, the pellets were suspended in the same Tris-HCl buffer solution. The suspension was divided into aliquots in 50 mL conical test tubes. After adding the glass beads, the cells were disrupted by vigorously vortexing with an interval of 30 seconds. The cell residues were removed by centrifuging at 3,000×g for 5 minutes. The supernatant was ultra-centrifuged at 130,000×g for 1 hour. The resultant pellets were collected and suspended in 50 mM Tris-HCl (pH 7.5) containing 33% glycerol, to a final volume of 1.6 mg/g (wet weight) of yeast used. The suspension was divided into aliquots and kept at −70° C. until it is used.

Test Example 3

In vitro Enzyme Assays for Chitin Synthase 1 of *Candida albicans* and Chitin Synthase 2 of *Saccharomyces cerevisiae*

The inhibitory activities against the chitin synthase 1 of *Candida albicans* chs2 Δ chs 3 Δ (abbreviated as 'enzyme 1') and the chitin synthase 2 of *Saccharomyces cerevisiae* ECY38-38A(pAS6) (abbreviated as 'enzyme 2') was examined for compound Nos. 1 to 70 compound and polyoxin D, a positive control compound. The result is given in Tables 1 to 3 below.

The inhibitory activity against the chitin synthase 1 prepared from *Candida albicans* and the chitin synthase 2 prepared from *Saccharomyces cerevisiae* were examined as follows. A reaction mixture containing 32 mM Tris-HCl (pH 7.5), 2 mM cobalt acetate, 1.1 mM UDP-[U-$^{14}$C]-N-acetyl-d-glucosamine (GlcNAc) (400,000 cpm/µmol), 2 µL of trypsin (0.75 mg/mL), 20 µL of each crude enzyme and 14 µL of each test sample was kept at 30° C. for 15 minutes to activate the enzyme. Then, 2 µL of trypsin inhibitor (1.5 mg/mL) was added and the mixture was kept in an ice bath for 10 minutes to deactivate trypsin. 2 µL of 0.8 M N-acetyl-d-glucosamine was added to a total volume of 50 µL and reaction was performed at 30° C. for 90 minutes. The reaction was stopped using 1 mL of 10% TCA solution and the reaction solution was filtered with a GF/C filter and dried at room temperature. After adding 3 mL of a scintillation cocktail solution, the amount of isotopes was measured using a liquid scintillation counter. Percentage inhibition against each enzyme was calculated by the following Equation 1.

$$\text{Inhibition (\%)} = \left[1 - \frac{\text{Sample (cpm)} - \text{Untreated (cpm)}}{\text{Control (cpm)} - \text{Untreated (cpm)}}\right] \times 100$$

The control group was not added with a test sample in the reaction mixture and that of the untreated group contained neither the test sample nor the crude enzyme.

The relative activities given in Tables 1 to 3 show the relative values of inhibitory activity of polyoxin D, which is known to have superior inhibitory activity against the aforementioned two enzymes. A 50% inhibitory activity of polyoxin D against the enzyme was given the value 5. A compound having the same inhibitory activity as that of polyoxin D at the same concentration was given the value 5. Compounds having the inhibitory activity at 2-fold, 4-fold, 8-fold and 16-fold higher concentrations than that of polyoxin D were given the values of 4, 3, 2 and 1, respectively. On the other hand, compounds having the inhibitory activity at ½, ¼ and ⅛ lower concentrations than that of polyoxin D were given the values of 6, 7 and 8, respectively.

TABLE 1

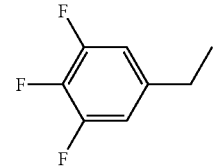

| Compound No. | $R_1$ | Relative activity Enzyme 2 | Enzyme 1 |
|---|---|---|---|
| 1 | 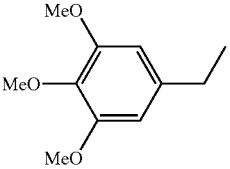 | 3 | 1 |
| 2 | 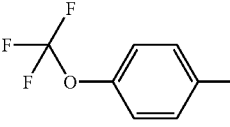 | 3 | 1 |
| 3 | 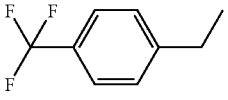 | 3 | 1 |
| 4 | 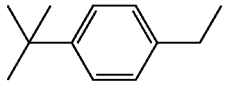 | 3 | 1 |
| 5 | 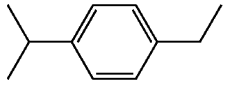 | 4 | 2 |
| 6 |  | 4 | 2 |

TABLE 2

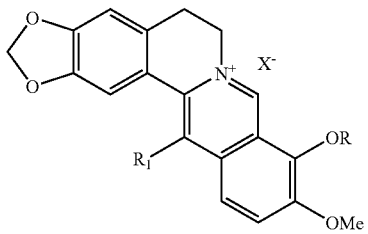

| Compound No. | R₁ | R | X— | Relative activity Enzyme 2 | Enzyme 1 |
|---|---|---|---|---|---|
| 7 | 4-tBu-benzyl | —CH₂CH₂CH₃ | I | 7 | 4 |
| 8 | 4-tBu-benzyl | —CH₂(CH₂)₂CH₃ | I | 7 | 4 |
| 9 | 4-tBu-benzyl | —CH₂(CH₂)₄CH₃ | I | 6 | 3 |
| 10 | 4-tBu-benzyl | —CH₂(CH₂)₆CH₃ | I | 5 | 3 |
| 11 | 4-tBu-benzyl | —CH₂CH₂CH₂OH | I | 6 | 4 |
| 12 | 4-tBu-benzyl | —CH₂(CH₂)₄CH₂Cl | I | 5 | 2 |
| 13 | 4-tBu-benzyl | —CH₂CH=CH₂ | I | 5 | 2 |
| 14 | 4-tBu-benzyl | —CH₂CH=CHCH₃ | Br | 5 | 2 |
| 15 | 4-tBu-benzyl | 4-tBu-benzyl | Br | 5 | 3 |
| 16 | 4-tBu-benzyl | 4-iPr-benzyl | Br | 5 | 3 |
| 17 | 4-iPr-benzyl | —CH₂CH₂CH₃ | I | 7 | 4 |
| 18 | 4-iPr-benzyl | —CH₂(CH₂)₂CH₃ | I | 7 | 4 |
| 19 | 4-iPr-benzyl | —CH₂(CH₂)₄CH₃ | I | 6 | 4 |

TABLE 2-continued
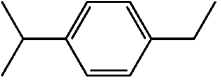
| Compound No. | R₁ | R | X— | Relative activity Enzyme 2 | Enzyme 1 |
|---|---|---|---|---|---|
| 20 | 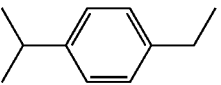 | —CH$_2$(CH$_2$)$_6$CH$_3$ | I | 5 | 3 |
| 21 | 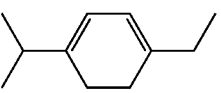 | —CH$_2$CH$_2$CH$_2$OH | I | 6 | 3 |
| 22 | 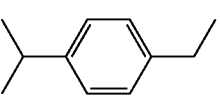 | —CH$_2$(CH$_2$)$_4$CH$_2$Cl | I | 5 | 2 |
| 23 | 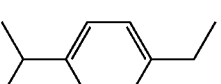 | —CH$_2$CH=CH$_2$ | I | 5 | 2 |
| 24 | 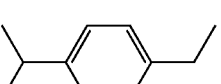 | —CH$_2$CH=CHCH$_3$ | Br | 5 | 2 |
| 25 | 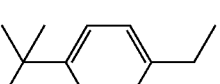 | 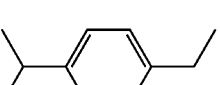 | Br | 5 | 2 |
| 26 | 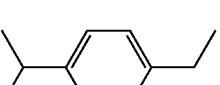 | 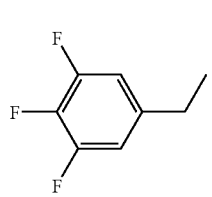 | Br | 5 | 2 |
| 27 | 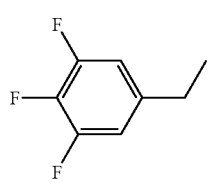 | —CH$_2$(CH$_2$)$_2$CH$_3$ | I | 6 | 3 |
| 28 | 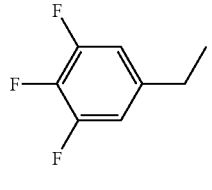 | —CH$_2$(CH$_2$)$_4$CH$_3$ | I | 5 | 2 |
| 29 | 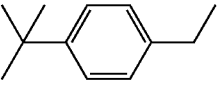 | 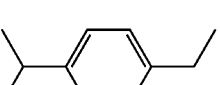 | Br | 5 | 2 |

TABLE 2-continued
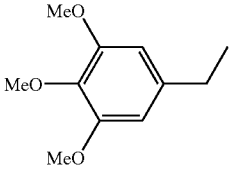
| Compound No. | R₁ | R | X— | Relative activity | |
|---|---|---|---|---|---|
| | | | | Enzyme 2 | Enzyme 1 |
| 30 | 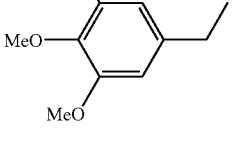 MeO, MeO, MeO | —CH₂(CH₂)₂CH₃ | I | 5 | 2 |
| 31 | 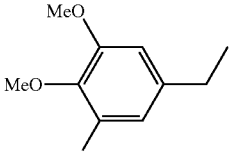 MeO, MeO, MeO | —CH₂(CH₂)₄CH₃ | I | 4 | 2 |
| 32 | 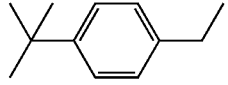 MeO, MeO, MeO | 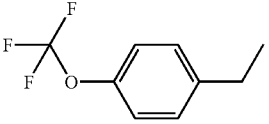 | Br | 4 | 2 |
| 33 | 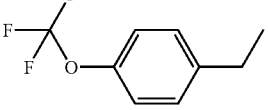 F₃CO— | —CH₂(CH₂)₂CH₃ | I | 6 | 3 |
| 34 | 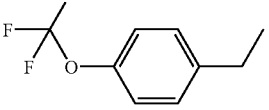 F₃CO— | —CH₂(CH₂)₄CH₃ | I | 5 | 2 |
| 35 | 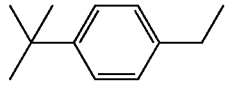 F₃CO— | 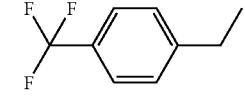 | Br | 5 | 2 |
| 36 | 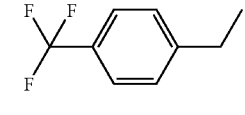 F₃C— | —CH₂(CH₂)₂CH₃ | I | 6 | 3 |
| 37 | 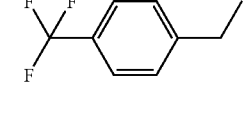 F₃C— | —CH₂(CH₂)₄CH₃ | I | 5 | 2 |
| 38 | 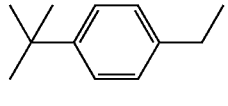 F₃C— | | Br | 5 | 2 |

TABLE 2-continued

[Structure: dibenzo[a,g]quinolizinium core with methylenedioxy group, R₁ substituent, OR group, and OMe group; counterion X⁻]

| Compound No. | R₁ | R | X— | Relative activity Enzyme 2 | Relative activity Enzyme 1 |
|---|---|---|---|---|---|
| 39 | 4-tert-butylbenzyl | —CH₂CH₂CH₃ | Cl | 7 | 4 |
| 40 | 4-tert-butylbenzyl | —CH₂(CH₂)₂CH₃ | Cl | 7 | 4 |
| 41 | 4-tert-butylbenzyl | —CH₂(CH₂)₄CH₃ | Cl | 6 | 4 |
| 41 | 4-tert-butylbenzyl | —CH₂(CH₂)₄CH₃ | Cl | 6 | 4 |
| 42 | 4-tert-butylbenzyl | —CH₂(CH₂)₆CH₃ | Cl | 6 | 3 |
| 43 | 4-tert-butylbenzyl | —CH₂CH₂CH₂OH | Cl | 7 | 4 |
| 44 | 4-tert-butylbenzyl | —CH₂(CH₂)₄CH₂Cl | Cl | 6 | 2 |
| 45 | 4-tert-butylbenzyl | —CH₂CH=CH₂ | Cl | 6 | 2 |
| 46 | 4-tert-butylbenzyl | —CH₂CH=CHCH₃ | Cl | 6 | 2 |
| 47 | 4-tert-butylbenzyl | 4-tert-butylbenzyl | Cl | 5 | 2 |
| 48 | 4-tert-butylbenzyl | 4-isopropylbenzyl | Cl | 5 | 2 |
| 49 | 4-isopropylbenzyl | —CH₂CH₂CH₃ | Cl | 7 | 4 |
| 50 | 4-isopropylbenzyl | —CH₂(CH₂)₂CH₃ | Cl | 7 | 4 |

TABLE 2-continued

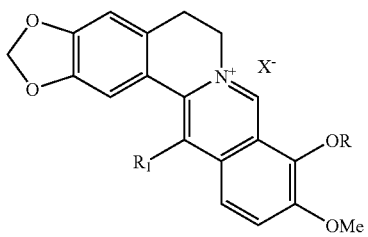

| Compound No. | R₁ | R | X— | Relative activity Enzyme 2 | Enzyme 1 |
|---|---|---|---|---|---|
| 51 | 4-isopropylphenyl-CH₂— | —CH₂(CH₂)₄CH₃ | Cl | 6 | 3 |
| 52 | 4-isopropylphenyl-CH₂— | —CH₂(CH₂)₆CH₃ | Cl | 6 | 2 |
| 53 | 4-isopropylphenyl-CH₂— | —CH₂CH₂CH₂OH | Cl | 6 | 4 |
| 54 | 4-isopropylphenyl-CH₂— | —CH₂(CH₂)₄CH₂Cl | Cl | 6 | 2 |
| 55 | 4-isopropylphenyl-CH₂— | —CH₂CH=CH₂ | Cl | 6 | 3 |
| 56 | 4-isopropylphenyl-CH₂— | —CH₂CH=CHCH₃ | Cl | 6 | 2 |
| 57 | 4-isopropylphenyl-CH₂— | 4-tert-butylphenyl-CH₂— | Cl | 5 | 2 |
| 58 | 4-isopropylphenyl-CH₂— | 4-isopropylphenyl-CH₂— | Cl | 5 | 2 |
| 59 | 3,4,5-trifluorophenyl-CH₂— | —CH₂(CH₂)₂CH₃ | Cl | 5 | 3 |
| 60 | 3,4,5-trifluorophenyl-CH₂— | —CH₂(CH₂)₄CH₃ | Cl | 5 | 2 |

TABLE 2-continued

|  |  |  |  | Relative activity | |
|---|---|---|---|---|---|
| Compound No. | $R_1$ | R | X— | Enzyme 2 | Enzyme 1 |
| 61 | 3,4,5-trifluorobenzyl | 4-tert-butylbenzyl | Cl | 4 | 2 |
| 62 | 3,4,5-trimethoxybenzyl | —CH$_2$(CH$_2$)$_2$CH$_3$ | Cl | 5 | 2 |
| 63 | 3,4,5-trimethoxybenzyl | —CH$_2$(CH$_2$)$_4$CH$_3$ | Cl | 4 | 2 |
| 64 | 3,4,5-trimethoxybenzyl | 4-tert-butylbenzyl | Cl | 4 | 2 |
| 65 | 4-(trifluoromethoxy)benzyl | —CH$_2$(CH$_2$)$_2$CH$_3$ | Cl | 6 | 3 |
| 66 | 4-(trifluoromethoxy)benzyl | —CH$_2$(CH$_2$)$_4$CH$_3$ | Cl | 5 | 2 |
| 67 | 4-(trifluoromethoxy)benzyl | 4-tert-butylbenzyl | Cl | 5 | 2 |
| 68 | 4-(trifluoromethyl)benzyl | —CH$_2$(CH$_2$)$_2$CH$_3$ | Cl | 6 | 3 |

TABLE 2-continued

[Structure: core berberine-type scaffold with methylenedioxy group, R₁ substituent, OR group, and OMe group, with X⁻ counterion]

| Compound No. | R₁ | R | X— | Relative activity Enzyme 2 | Relative activity Enzyme 1 |
|---|---|---|---|---|---|
| 69 | 4-(trifluoromethyl)benzyl (F₃C-C₆H₄-CH₂-) | —CH₂(CH₂)₄CH₃ | Cl | 5 | 3 |
| 70 | 4-(trifluoromethyl)benzyl | 4-tert-butylbenzyl | Cl | 5 | 2 |

TABLE 3

| Comparative compounds | Relative activity Enzyme 2 | Relative activity Enzyme 1 |
|---|---|---|
| Comparative compound 1 [structure with methylenedioxy, two OCH₃ groups, and 4-tert-butylbenzyl substituent; Cl⁻] (KR258849, Example 40) | 3 | 1 |
| Comparative compound 2 [structure with methylenedioxy, two OCH₃ groups, and 4-(trifluoromethyl)benzyl substituent; Cl⁻] (KR258849, Example 26) | 2 | <1 |

TABLE 3-continued

| Comparative compounds | Relative activity | |
|---|---|---|
| | Enzyme 2 | Enzyme 1 |
| Comparative compound 3 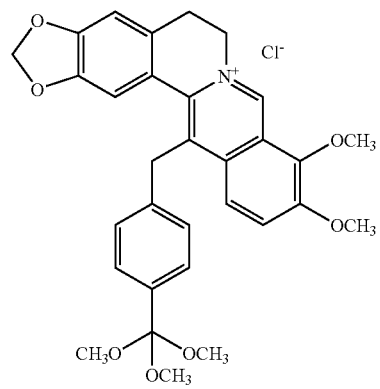 (KR258849, Example 29) | 1 | <1 |

Test Example 4

Antifungal Activity Against Human Pathogenic Fungi

In vitro antifungal activity (MIC) against human pathogenic fungi was examined for the compounds that showed potent inhibitory activities against the chitin synthases and amphotericin B, a control compound. The result is given in Table 4 below.

Candida albicans ATCC 10231, Candida lusitaniae ATCC 42720, Candida krusei ATCC 6258, Candida tropicalis ATCC 13803, Candida glabrata ATCC 48435, Candida parapsilosis ATCC 34136, Cryptococcus neoformans ATCC 36556, Aspergillus fumigatus ATCC 16424, Aspergillus flavus ATCC 64025, Aspergillus terreus ATCC 46941 and Mucor ramosissimus ATCC 90286 strains for the MIC (minimum inhibitory concentration) measurement were obtained from ATCC (American Type Culture Collection) in the U.S. The Candida albicans A207(clinical isolate) strain was used by isolating it from the patients.

The determination of MIC was performed according to the NCCLS (National Committee for Clinical Laboratory Standard) method. Each test sample solution was diluted two-fold and inoculated with a fungal suspension to reach a final inoculum size of $5 \times 10^2$ to $2.5 \times 10^3$ cell/mL. The Cryptococcus neoformans strain was cultured in the RPMI 1640 medium for 72 hours. Other strains were cultured for 48 hours. MIC was determined as the lowest concentration of the compound that completely inhibited the growth of the fungi by comparing with a control not containing the compound.

TABLE 4

| Human pathogenic fungi | MIC (minimum inhibitory concentration) (Unit: µg/mL) | | | | | | | | |
|---|---|---|---|---|---|---|---|---|---|
| | Compd. No. 7 | Compd. No. 8 | Compd. No. 9 | Compd. No. 10 | Compd. No. 11 | Compd. No. 12 | Compd. No. 13 | Compd. No. 14 | amphotericin B |
| Candida albicans ATCC 10231 | 1 | 0.5 | 0.25 | 0.25 | 0.5 | 0.5 | 1 | 0.5 | 0.5 |
| Candida albicans A207 (clinical isolate) | 1 | 0.5 | 0.25 | 0.25 | 0.5 | 0.5 | 1 | 0.5 | 0.5 |
| Candida tropicalis ATCC 13803 | 0.5 | 0.25 | 0.125 | 0.125 | 0.5 | 0.5 | 1 | 0.5 | 0.5 |
| Candida lusitaniae ATCC 42720 | 2 | 1 | 1 | 0.5 | 2 | 2 | 2 | 1 | 1 |
| Candida krusei ATCC 6258 | 2 | 2 | 1 | 1 | 1 | 1 | 2 | 1 | 0.5 |
| Candida glabrata ATCC 48435 | 4 | 4 | 2 | 2 | 2 | 2 | 8 | 4 | 1 |
| Candida parapsilosis ATCC 34136 | 4 | 4 | 2 | 2 | 2 | 2 | 4 | 4 | 0.5 |
| Cryptococcus neoformans ATCC 36556 | 2 | 1 | 1 | 1 | 1 | 1 | 2 | 1 | 0.125 |
| Aspergillus fumigatus ATCC 16424 | 4 | 2 | 2 | 2 | 2 | 2 | 8 | 2 | 1 |
| Aspergillus terreus ATCC 46941 | 8 | 8 | 8 | 4 | 8 | 8 | 8 | 4 | 16 |
| Aspergillus flavus ATCC 64025 | 8 | 8 | 8 | 4 | 8 | 8 | 8 | 8 | 4 |
| Mucor ramosissimus ATCC 90286 | 4 | 4 | 4 | 2 | 4 | 4 | 4 | 4 | 0.5 |

TABLE 4-continued

| Human pathogenic fungi | MIC (minimum inhibitory concentration) (Unit: μg/mL) | | | | | | | | |
|---|---|---|---|---|---|---|---|---|---|
| | Compd. No. 15 | Compd. No. 16 | Compd. No. 17 | Compd. No. 18 | Compd No. 19 | Compd No. 20 | Compd. No. 21 | Compd. No. 22 | Amphotericin B |
| *Candida albicans* ATCC 10231 | 1 | 1 | 1 | 0.5 | 0.25 | 0.25 | 0.5 | 0.5 | 0.5 |
| *Candida albicans* A207 (Clinical isolate) | 1 | 1 | 1 | 0.5 | 0.25 | 0.25 | 0.5 | 0.5 | 0.5 |
| *Candida tropicalis* ATCC 13803 | 1 | 1 | 0.5 | 0.25 | 0.125 | 0.125 | 0.5 | 0.5 | 0.5 |
| *Candida lusitaniae* ATCC 42720 | 4 | 4 | 2 | 1 | 1 | 0.5 | 2 | 2 | 1 |
| *Candida krusei* ATCC 6258 | 4 | 2 | 2 | 1 | 1 | 1 | 1 | 1 | 0.5 |
| *Candida glabrata* ATCC 48435 | 4 | 2 | 4 | 4 | 2 | 2 | 2 | 2 | 1 |
| *Candida parapsilosis* ATCC 34136 | 8 | 8 | 4 | 4 | 2 | 2 | 2 | 2 | 0.5 |
| *Cryptococcus neoformans* ATCC 36556 | 2 | 2 | 2 | 1 | 1 | 1 | 1 | 1 | 0.125 |
| *Aspergillus fumigatus* ATCC 16424 | 4 | 4 | 4 | 2 | 2 | 2 | 2 | 2 | 1 |
| *Aspergillus terreus* ATCC 46941 | 8 | 8 | 8 | 8 | 8 | 4 | 8 | 8 | 16 |
| *Aspergillus flavus* ATCC 64025 | 8 | 8 | 8 | 8 | 8 | 4 | 8 | 8 | 4 |
| *Mucor ramosissimus* ATCC 90286 | 8 | 8 | 4 | 4 | 4 | 2 | 4 | 4 | 0.5 |

| Human pathogenic fungi | MIC (minimum inhibitory concentration) (Unit: μg/mL) | | | | | | | | |
|---|---|---|---|---|---|---|---|---|---|
| | Compd. No. 23 | Compd. No. 24 | Compd. No. 25 | Compd. No. 26 | Compd. No. 39 | Compd No. 40 | Compd. No. 41 | Compd. No. 42 | Amphotericin B |
| *Candida albicans* ATCC 10231 | 1 | 0.5 | 1 | 1 | 1 | 0.5 | 0.25 | 0.25 | 0.5 |
| *Candida albicans* A207 (clinical isolate) | 1 | 0.5 | 1 | 1 | 1 | 0.5 | 0.25 | 0.25 | 0.5 |
| *Candida tropicalis* ATCC 13803 | 1 | 0.5 | 1 | 1 | 0.5 | 0.25 | 0.125 | 0.125 | 0.5 |
| *Candida lusitaniae* ATCC 42720 | 2 | 1 | 4 | 4 | 1 | 0.5 | 0.5 | 0.5 | 1 |
| *Candida krusei* ATCC 6258 | 2 | 1 | 4 | 2 | 2 | 1 | 1 | 1 | 0.5 |
| *Candida glabrata* ATCC 48435 | 8 | 4 | 4 | 2 | 4 | 4 | 2 | 1 | 1 |
| *Candida parapsilosis* ATCC 34136 | 4 | 4 | 8 | 8 | 4 | 4 | 2 | 1 | 0.5 |
| *Cryptococcus neoformans* ATCC 36556 | 2 | 1 | 2 | 2 | 2 | 1 | 0.5 | 0.5 | 0.125 |
| *Aspergillus fumigatis* ATCC 16424 | 8 | 2 | 4 | 4 | 4 | 2 | 2 | 2 | 1 |
| *Aspergillus terreus* ATCC 46941 | 8 | 4 | 8 | 8 | 8 | 8 | 8 | 4 | 16 |
| *Aspergillus flavus* ATCC 64025 | 8 | 8 | 8 | 8 | 8 | 8 | 8 | 4 | 4 |
| *Mucor ramosissimus* ATCC 90286 | 4 | 4 | 8 | 8 | 4 | 4 | 4 | 2 | 0.5 |

| Human pathogenic fungi | MIC (minimum inhibitory concentration) (Unit: μg/mL) | | | | | | | | |
|---|---|---|---|---|---|---|---|---|---|
| | Compd. No. 43 | Compd. No. 44 | Compd. No. 45 | Compd. No. 46 | Compd. No. 47 | Compd. No. 48 | Compd. No. 49 | Compd. No. 50 | Amphotericin B |
| *Candida albicans* ATCC 10231 | 0.5 | 0.5 | 1 | 0.5 | 1 | 1 | 1 | 0.5 | 0.5 |
| *Candida albicans* A207 (clinical isolate) | 0.5 | 0.5 | 1 | 0.5 | 1 | 1 | 1 | 0.5 | 0.5 |
| *Candida tropicalis* ATCC 13803 | 0.5 | 0.5 | 1 | 0.5 | 1 | 1 | 0.5 | 0.25 | 0.5 |
| *Candida lusitaniae* ATCC 42720 | 2 | 2 | 2 | 1 | 4 | 4 | 1 | 0.5 | 1 |
| *Candida krusei* ATCC 6258 | 1 | 1 | 2 | 1 | 4 | 2 | 2 | 1 | 0.5 |
| *Candida glabrata* ATCC 48435 | 2 | 2 | 8 | 4 | 4 | 2 | 4 | 4 | 1 |

TABLE 4-continued

| Human pathogenic fungi | | | | | | | | | | |
|---|---|---|---|---|---|---|---|---|---|---|
| Candida parapsilosis ATCC 34136 | 2 | 2 | 4 | 4 | 8 | 8 | 4 | 4 | 0.5 | |
| Cryptococcus neoformans ATCC 36556 | 1 | 1 | 2 | 1 | 2 | 2 | 2 | 1 | 0.125 | |
| Aspergillus fumigatus ATCC 16424 | 2 | 2 | 8 | 2 | 4 | 4 | 4 | 2 | 1 | |
| Aspergillus terreus ATCC 46941 | 8 | 8 | 8 | 4 | 8 | 8 | 8 | 8 | 16 | |
| Aspergillus flavus ATCC 64025 | 8 | 8 | 8 | 8 | 8 | 8 | 8 | 8 | 4 | |
| Mucor ramosissimus ATCC 90286 | 4 | 4 | 4 | 4 | 8 | 8 | 4 | 4 | 0.5 | |

| | MIC (minimum inhibitory concentration) (Unit: µg/mL) | | | | | | | | | |
|---|---|---|---|---|---|---|---|---|---|---|
| Human pathogenic fungi | Compd. No. 51 | Compd. No. 52 | Compd. No. 53 | Compd. No. 54 | Compd. No. 55 | Compd. No. 56 | Compd. No. 57 | Compd. No. 58 | Compd. No. B | Comp. Compd. No. 1 |
| Candida albicans ATCC 10231 | 0.25 | 0.25 | 0.5 | 0.5 | 1 | 0.5 | 1 | 1 | 0.5 | 4 |
| Candida albicans A207 (Clinical isolate) | 0.25 | 0.25 | 0.5 | 0.5 | 1 | 0.5 | 1 | 1 | 0.5 | 8 |
| Candida tropicalis ATCC 13803 | 0.125 | 0.125 | 0.5 | 0.5 | 1 | 0.5 | 1 | 1 | 0.5 | 2 |
| Candida lusitaniae ATCC 42720 | 0.5 | 0.5 | 2 | 2 | 2 | 1 | 4 | 4 | 1 | 8 |
| Candida krusei ATCC 6258 | 1 | 1 | 1 | 1 | 2 | 1 | 4 | 2 | 0.5 | 16 |
| Candida glabrata ATCC 48435 | 2 | 1 | 2 | 2 | 8 | 4 | 4 | 2 | 1 | >128 |
| Candida parapsilosis ATCC 34136 | 2 | 1 | 2 | 2 | 4 | 4 | 8 | 8 | 0.5 | >128 |
| Cryptococcus neoformans ATCC 36556 | 0.5 | 0.5 | 1 | 1 | 2 | 1 | 2 | 2 | 0.125 | 8 |
| Aspergillus fumigatus ATCC 16424 | 2 | 2 | 2 | 2 | 8 | 2 | 4 | 4 | 1 | 128 |
| Aspergillus terreus ATCC 46941 | 8 | 4 | 8 | 8 | 8 | 4 | 8 | 8 | 16 | >128 |
| Aspergillus flavus ATCC 64025 | 8 | 4 | 8 | 8 | 8 | 8 | 8 | 8 | 4 | >128 |
| Mucor ramosissimus ATCC 90286 | 4 | 2 | 4 | 4 | 4 | 4 | 8 | 8 | 0.5 | 128 |

The novel compounds in accordance with the present invention were confirmed to have superior antifungal activity. In particular, when compared with the compound having the best activity of those disclosed in Korean Patent No. 258,849 (Comparative Compound No. 1; tert-butyl benzyl group is introduced at the C-13 position of berberine having methoxy groups at the C-9 and C-10 positions), the compounds of the present invention in which a methoxy group is introduced at the C-10 position and a relatively long $C_3$-$C_{10}$ alkoxy chain is introduced at the C-9 position showed 10-fold or more of antifungal activities against most of the 12 human pathogenic fungi. In some strains, the antifungal activity was 32 to 64-fold more potent. In particular, whereas the compound disclosed in Korean Patent No. 258,849 (Comparative Compound No. 1) showed no antifungal activities against the *Candida glabrata* and *Candida parapsilosis* strains at all, the compound of the present invention showed 128-fold or more of antifungal activities. Furthermore, the antifungal activity against the *Aspergillus* strain, which has drawn a lot of concerns recently, was 32 to 64-fold or better.

Test Example 5

Acute Oral Toxicity

Toxicity of compound No. 8, which shows a potent inhibitory effect against the chitin synthases and fungi and has the solubility adequate for the toxicity test, and compound No. 50, which has been transferred from iodide to chloride to improve the solubility, was examined on mice. Each compound was suspended in 1% carboxymethylcellulose (CMC), and orally and abdominally administered to 6-week-old male ICR mice. General symptoms, weight change and deaths were observed for a week under normal breeding condition. Then, an autopsy was performed on the mice. The results are given in Table 5 below.

TABLE 5

| | Acute toxicity (mg/kg) | | | | |
|---|---|---|---|---|---|
| Test compounds | Test animal | Administration route | Sex | $LD_{50}$ | Autopsy findings |
| Compound No. 8 | ICR mouse | Oral | Male | >1000 | Nothing abnormal |
| Compound No. 8 | ICR mouse | Abdominal | Male | >15 | Nothing abnormal |
| Compound No. 50 | ICR mouse | Oral | Male | >1000 | Nothing abnormal |
| Compound No. 50 | ICR mouse | Abdominal | Male | >15 | Nothing abnormal |

Of the compounds in accordance with the present invention, the iodides compound Nos. 7, 8, 17 and 18 and the chlorides compound Nos. 39, 40, 49 and 50 showed superior inhibitory activities against the chitin synthases, which are essential in the growth of fungi. And, the MICs of the iodides compound Nos. 7, 8, 17 and 18 and the chlorides compound Nos. 39, 40, 49 and 50 showed 500-1,000 times or more of antifungal activities than that of the berberrubine, the starting material (MIC=256-512 μg/mL).

INDUSTRIAL APPLICABILITY

Since fungi are eukaryotic organisms, most of conventional antifungal agents are toxic to human. However, because chitin synthase is an essential enzyme present only in fungi, a selective antifungal activity may be attained without human toxicity if the activity of the enzyme can be inhibited effectively. Most of the compounds of the present invention showed superior inhibitory activities against chitin synthase. Among them, compounds Nos. 7, 8, 17, 18, 39, 40, 49 and 50 showed exceptionally superior inhibitory activities. Also, they showed antifungal activities comparable to that of amphotericin B, which is an antifungal agent used to treat systemic fungal infection. In toxicity test with mice, compound No. 8 showed no abnormalities in general symptoms and body weight with the oral administration dosage of 1,000 mg/kg. And there was no case of death observed. Accordingly, the compounds in accordance with the present invention have superior inhibitory activities against chitin synthase, antifungal activities comparable to that of amphotericin B, with less toxicity.

Those skilled in the art will appreciate that the concepts and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the present invention as set forth in the appended claims.

The invention claimed is:

1. A berberrubine derivative represented by the following formula (1) or a pharmaceutically acceptable salt thereof:

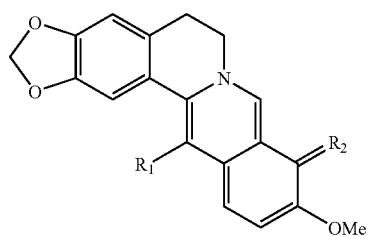

(1)

wherein $R_1$ is benzyl or substituted benzyl; $R_2$ is ketone (=O) or OR, wherein R is $C_3$-$C_{10}$ alkyl, $C_1$-$C_{10}$ haloalkyl, $C_1$-$C_{10}$ hydroxyalkyl, $C_2$-$C_{10}$ alkenyl, benzyl or substituted benzyl; and the substituted benzyl has 1 to 4 substituents selected from halogen atom, $C_1$-$C_6$ alkyl, $C_1$-$C_6$ haloalkyl, $C_1$-$C_6$ alkoxy and $C_1$-$C_6$ haloalkoxy.

2. The compound as set forth in claim 1, wherein $R_1$ is benzyl or substituted benzyl having 1 to 4 substituents selected from halogen, $C_1$-$C_6$ alkyl, $C_1$-$C_6$ haloalkyl, $C_1$-$C_6$ alkoxy and $C_1$-$C_6$ haloalkoxy; and $R_2$ is ketone (=O) or OR, wherein R is $C_6$-$C_{10}$ alkyl, $C_1$-$C_6$ haloalkyl, $C_1$-$C_6$ hydroxyalkyl, $C_2$-$C_6$ alkenyl, benzyl or substituted benzyl with $C_1$-$C_6$ alkyl.

3. The compound as set forth in claim 1, wherein the pharmaceutically acceptable salt is a halide or an acid adduct of an inorganic acid or organic acid.

4. The compound as set forth in claim 1, which is selected from the group consisting of
13-(3,4,5-trifluorobenzyl)berberrubine (Compound No. 1),
13-(3,4,5-trimethoxybenzyl)berberrubine (Compound No. 2),
13-(4-trifluoromethoxybenzyl)berberrubine (Compound No. 3),
13-(4-trifluoromethylbenzyl)berberrubine (Compound No. 4),
13-(4-tert-butylbenzyl)berberrubine (Compound No. 5),
13-(4-isopropylbenzyl)berberrubine (Compound No. 6),
13-(4-tert-butylbenzyl)-9-O-propylberberrubine iodide (Compound No. 7),
13-(4-tert-butylbenzyl)-9-O-butylberberrubine iodide (Compound No. 8),
13-(4-tert-butylbenzyl)-9-O-hexylberberrubine iodide (Compound No. 9),
13-(4-tert-butylbenzyl)-9-O-octylberberrubine iodide (Compound No. 10),
13-(4-tert-butylbenzyl)-9-O-(3-hydroxypropyl)berberrubine iodide (Compound No. 11),
13-(4-tert-butylbenzyl)-9-O-(6-chlorohexyl)berberrubine iodide (Compound No. 12),
13-(4-tert-butylbenzyl)-9-O-allylberberrubine iodide (Compound No. 13),
13-(4-tert-butylbenzyl)-9-O-crotylberberrubine bromide (Compound No. 14),
13-(4-tert-butylbenzyl)-9-O-(4-tert-butylbenzyl)berberrubine bromide (Compound No. 15),
13-(4-tert-butylbenzyl)-9-O-(4-isopropylbenzyl)berberrubine bromide (Compound No. 16),
13-(4-isopropylbenzyl)-9-O-propylberberrubine iodide (Compound No. 17),
13-(4-isopropylbenzyl)-9-O-butylberberrubine iodide (Compound No. 18),
13-(4-isopropylbenzyl)-9-O-hexylberberrubine iodide (Compound No. 19),
13-(4-isopropylbenzyl)-9-O-octylberberrubine iodide (Compound No. 20),
13-(4-isopropylbenzyl)-9-O-(3-hydroxypropyl)berberrubine iodide (Compound No. 21),
13-(4-isopropylbenzyl)-9-O-(6-chlorohexyl)berberrubine iodide (Compound No. 22),
13-(4-isopropylbenzyl)-9-O-allylberberrubine iodide (Compound No. 23),
13-(4-isopropylbenzyl)-9-O-crotylberberrubine bromide (Compound No. 24),
13-(4-isopropylbenzyl)-9-O-(4-tert-butylbenzyl)berberrubine bromide (Compound No. 25),
13-(4-isopropylbenzyl)-9-O-(4-isopropylbenzyl)berberrubine bromide (Compound No. 26),
13-(3,4,5-trifluorobenzyl)-9-O-butylberberrubine iodide (Compound No. 27),
13-(3,4,5-trifluorobenzyl)-9-O-hexylberberrubine iodide (Compound No. 28),
13-(3,4,5-trifluorobenzyl)-9-O-(4-tert-butylbenzyl)berberrubine bromide (Compound No. 29),
13-(3,4,5-trimethoxybenzyl)-9-O-butylberberrubine iodide (Compound No. 30),
13-(3,4,5-trimethoxybenzyl)-9-O-hexylberberrubine iodide (Compound No. 31),
13-(3,4,5-trimethoxybenzyl)-9-O-(4-tert-butylbenzyl)berberrubine bromide(32),
13-(4-trifluoromethoxybenzyl)-9-O-butylberberrubine iodide (Compound No. 33), 13-(4-trifluoromethoxybenzyl)-9-O-hexylberberrubine iodide (Compound No. 34),
13-(4-trifluoromethoxybenzyl)-9-O-(4-tert-butylbenzyl)berberrubine bromide (Compound No. 35),
13-(4-trifluoromethylbenzyl)-9-O-butylberberrubine iodide (Compound No. 36),
13-(4-trifluoromethylbenzyl)-9-O-hexylberberrubine iodide (Compound No. 37),
13-(4-trifluoromethylbenzyl)-9-O-(4-tert-butylbenzyl)berberrubine bromide (Compound No. 38),
13-(4-tert-butylbenzyl)-9-O-propylberberrubine chloride (Compound No. 39),
13-(4-tert-butylbenzyl)-9-O-butylberberrubine chloride (Compound No. 40),
13-(4-tert-butylbenzyl)-9-O-hexylberberrubine chloride (Compound No. 41),
13-(4-tert-butylbenzyl)-9-O-octylberberrubine chloride (Compound No. 42),
13-(4-tert-butylbenzyl)-9-O-(3-hydroxypropyl)berberrubine chloride (Compound No. 43),
13-(4-tert-butylbenzyl)-9-O-(6-chlorohexyl)berberrubine chloride (Compound No. 44),
13-(4-tert-butylbenzyl)-9-O-allylberberrubine chloride (Compound No. 45),
13-(4-tert-butylbenzyl)-9-O-crotylberberrubine chloride (Compound No. 46),
13-(4-tert-butylbenzyl)-9-O-(4-tert-butylbenzyl)berberrubine chloride (Compound No. 47),
13-(4-tert-butylbenzyl)-9-O-(4-isopropylbenzyl)berberrubine chloride (Compound No. 48),
13-(4-isopropylbenzyl)-9-O-propylberberrubine chloride (Compound No. 49),
13-(4-isopropylbenzyl)-9-O-butylberberrubine chloride (Compound No. 50),
13-(4-isopropylbenzyl)-9-O-hexylberberrubine chloride (Compound No. 51),
13-(4-isopropylbenzyl)-9-O-octylberberrubine chloride (Compound No. 52),
13-(4-isopropylbenzyl)-9-O-(3-hydroxypropyl)berberrubine chloride (Compound No. 53),
13-(4-isopropylbenzyl)-9-O-(6-chlorohexyl)berberrubine chloride (Compound No. 54),
13-(4-isopropylbenzyl)-9-O-allylberberrubine chloride (Compound No. 55),
13-(4-isopropylbenzyl)-9-O-crotylberberrubine chloride (Compound No. 56),
13-(4-isopropylbenzyl)-9-O-(4-tert-butylbenzyl)berberrubine chloride (Compound No. 57),
13-(4-isopropylbenzyl)-9-O-(4-isopropylbenzyl)berberrubine chloride (Compound No. 58),
13-(3,4,5-trifluorobenzyl)-9-O-butylberberrubine chloride (Compound No. 59),
13-(3,4,5-trifluorobenzyl)-9-O-hexylberberrubine chloride (Compound No. 60),
13-(3,4,5-trifluorobenzyl)-9-O-(4-tert-butylbenzyl)berberrubine chloride (Compound No. 61),
13-(3,4,5-trimethoxybenzyl)-9-O-butylberberrubine chloride (Compound No. 62),
13-(3,4,5-trimethoxybenzyl)-9-O-hexylberberrubine chloride (Compound No. 63),
13-(3,4,5-trimethoxybenzyl)-9-O-(4-tert-butylbenzyl)berberrubine chloride (Compound No. 64),
13-(4-trifluoromethoxybenzyl)-9-O-butylberberrubine chloride (Compound No. 65),
13-(4-trifluoromethoxybenzyl)-9-O-hexylberberrubine chloride (Compound No. 66),
13-(4-trifluoromethoxybenzyl)-9-O-(4-tert-butylbenzyl)berberrubine chloride (Compound No. 67),
13-(4-trifluoromethylbenzyl)-9-O-butylberberrubine chloride (Compound No. 68),
13-(4-trifluoromethylbenzyl)-9-O-hexylberberrubine chloride (Compound No. 69),
13-(4-trifluoromethylbenzyl)-9-O-(4-tert-butylbenzyl)berberrubine chloride (Compound No. 70) and pharmaceutically acceptable salts thereof.

5. A pharmaceutical composition comprising the compound as set forth in any one of the aforementioned claims 1 to 4 as an active ingredient.

6. The pharmaceutical composition as set forth in claim 5, which is prepared in the form selected from a tablet, a capsule, a syrup, an injection, a suppository, an ointment, a cream, a lotion and a liquid.

* * * * *